US008267046B2

(12) United States Patent
Benabdelmouna et al.

(10) Patent No.: US 8,267,046 B2
(45) Date of Patent: Sep. 18, 2012

(54) PRODUCTION OF BIVALVE TETRAPLOID MOLLUSKS FROM DIPLOID PARENTS

(75) Inventors: Abdellah Benabdelmouna, Rochefort (FR); Christophe Ledu, La Tremblade (FR)

(73) Assignee: Institut Francais de la Recherche pour l'Exploration de la Mer (Ifremer), Issy les Moulineaux (FR)

( * ) Notice: Subject to any disclaimer, the term of this patent is extended or adjusted under 35 U.S.C. 154(b) by 305 days.

(21) Appl. No.: 12/532,725

(22) PCT Filed: Mar. 19, 2008

(86) PCT No.: PCT/FR2008/000362
§ 371 (c)(1),
(2), (4) Date: Oct. 27, 2009

(87) PCT Pub. No.: WO2008/132350
PCT Pub. Date: Nov. 6, 2008

(65) Prior Publication Data
US 2010/0107987 A1  May 6, 2010

(30) Foreign Application Priority Data
Mar. 23, 2007 (FR) ..................... 07 02123

(51) Int. Cl.
*A01K 61/00* (2006.01)
(52) U.S. Cl. ..................... 119/234; 119/236
(58) Field of Classification Search ........... 119/234, 119/236, 237, 304, 308
See application file for complete search history.

(56) References Cited

U.S. PATENT DOCUMENTS
5,824,841 A * 10/1998 Guo et al. ........... 800/8

FOREIGN PATENT DOCUMENTS
WO    WO 95/19703    7/1995

OTHER PUBLICATIONS

McCombie et al.,"A Complimentary Method for Production of Tetraploid Crassostrea giga Using Crosses between Diploids and Tetraploids with Cytochalasin B Treatments", Marine Biotechnology, vol. 7, 2005, pp. 318-330.*
Guo, et al., "Genetic Consequences of Blocking Polar Body I with Cytochalasin B in Fertilized Eggs of the Pacific Oyster, *Cassostrea gigas*: I. Ploidy of Resultant Embryos", Biol. Bull. 183:3, 1992, pp. 381-386.
Scarpa, et al., "Induction of Tetraploidy in Mussels by Suppression of Polar Body Formation", Nippon Suisan Gakkaishi, 59:12, 1993, pp. 2017-2023.
Peruzzi, et al., "Tetraploid Induction by Meiosis Inhibition with Cytochalasin B in the Dwarf Surfclam, *Mulinia lateralis* Say: Effects of Temperature", Journal of Shellfish Research, 21:2, 2002, pp. 667-684.
Guo, et al., "Viable Tetraploids in the Pacific Oyster (*Crassostrea gigas thunberg*) Produced by Inhibiting Polar Body 1 in Eggs from Triploids", Molecular Marine Biology and Biotechnology, 3:1, 1994, pp. 42-50.

* cited by examiner

*Primary Examiner* — Kimberly Berona
*Assistant Examiner* — Danielle Clerkley
(74) *Attorney, Agent, or Firm* — Morgan, Lewis & Bockius LLP

(57) ABSTRACT

The invention relates to a method for producing viable tetraploid bivalve mollusks, by fertilisation of diploid female ovocytes with diploid male sperm, followed by the induction of the retention of the first polar body of the fertilised eggs, isolation from the obtained larvae of a larval sub-population enriched in tetraploids and selective raising of said sub-population.

11 Claims, 20 Drawing Sheets

PRODUCTION OF BIVALVE TETRAPLOID MOLLUSKS FROM DIPLOID PARENTS

RELATED APPLICATIONS

The present application is a U.S. National Phase Application of International Application PCT/FR2008/000362, filed Mar. 19, 2008, which claims the benefit of French Application No. 0702123, filed Mar. 23, 2007, 2006, all of which are herein incorporated by reference in their entirety.

The present invention relates to the production of viable tetraploid bivalve mollusks.

The production of polyploid bivalves is currently of considerable interest, especially with regard to oysters.

In fact, triploid oysters, also called "four-season oysters" offer several advantages. As they have an odd number of chromosomes they are normally sterile, which means that on the one hand they can have faster growth (their energy being used for growth rather than for reproduction), and on the other hand they do not produce milt during the summer months, which means they are of constant quality all year round.

Triploid oysters can be obtained by crossing diploid parents, followed by retention of the first or second polar body by chemical treatment, generally with cytochalasin B (CB) or optionally with 6-dimethyl-aminopurine (6-DMAP), or by physical treatment (notably thermal shock or pressure). However, these two techniques have a certain number of drawbacks. Notably we may mention a lack of uniformity in level of ploidy; in fact, the treatments inducing retention of the polar bodies result in mixed larval populations, possessing varied levels of ploidy. At the end of larval development, the population obtained generally contains at most 90% of triploid individuals, the rest of the population being constituted of diploids. Moreover, in the case of chemical treatments, those that make use of very toxic products are poorly perceived by the public, and necessitate constant application of strict precautions to avoid any danger for the handlers.

That is why the method currently preferred for the production of triploid oysters consists of crossing tetraploid oysters with diploid oysters. Apart from the advantage of not requiring repeated recourse to chemical treatments, this method offers the advantage of obtaining a homogeneous population, all the individuals of which are triploid. The main drawback of this method arises from the difficulty of obtaining viable tetraploid parents.

The production of tetraploid larvae, in variable proportions, has been observed in the course of experiments for production of triploids by crossing diploid parents and retention of expulsion of the first polar body by treatment with cytochalasin B (CB). However, this production of tetraploid larvae appears to be transient; it has only been described during the first 24 hours post-fertilization (STEPHENS & DOWNING, J. Shellfish Res, 7, 550-51, 1988; GUO et al., Biol. Bull., 183, 381-93, 1992). The proportion of tetraploid larvae detected drops dramatically, so that no tetraploid larva is detected during the rest of larval breeding or at the moment of settlement and especially during breeding in the micronursery or nursery.

Two hypotheses have been put forward to explain the failure of all the approaches used for obtaining viable tetraploids directly from diploid parents:

According to the first of these hypotheses, tetraploidy would involve a genetic burden incompatible with the survival of the larvae owing to expression of certain recessive lethal alleles whose copy number becomes changed following tetraploidization (hypothesis of recessive lethal alleles). However, experiments in gynogenesis using consanguineous and wild-type lines tend to show expression of recessive lethal alleles cannot on their own explain all of the mortality of the tetraploids during the larval stage (GUO, PhD Dissertation: Studies on tetraploid induction in the Pacific oyster, Crassostrea gigas., University of Washington, Seattle 1991).

According to the second of these hypotheses (hypothesis of the nucleo-cytoplasmic ratio), the oocytes produced by diploid female parents are too small to support a nucleus whose genetic material is doubled following tetraploidization. This second hypothesis was preferred, and formed the basis for developing the methods proposed to date for obtaining viable tetraploid oysters.

The first method to have been applied successfully consists of crossing triploid female parents with diploid male parents, and blocking the first phase of meiosis (MI) by inducing the retention of the first polar body (PCT Application WO 95/19703; GUO & ALLEN, Mol Mar Biol Biotechnol 3, 42-50, 1994). This method is based on the fact that the few rare triploid females that are not sterile produce oocytes that are much larger than the oocytes produced by the diploid females, so that they are able to support a tetraploid nucleus.

Recently, the production of viable tetraploid oysters by crossing tetraploid males with diploid females, previously selected for large size of their oocytes, followed by retention of the second polar body has also been described (MCCOMBIE et al., Mar Biotechnol (NY), 7, 318-30, 2005). However, at the present time, the only method of production of tetraploids used in practice is crossing triploid females with diploid males. However, this method has two major drawbacks:

1) As these tetraploids are obtained from triploids with appreciable fertility, the use of these same tetraploids for producing new generations of triploids may lead to an increase in fertility of the triploids obtained from successive generations. Thus, the average fertility was observed to increase from 2% for the first-generation triploids ("chemical" triploids obtained after retention of the second PB following treatment with CB) to 13.4% for the second-generation triploids, resulting from crossing tetraploid male parents with diploid females (GUO & ALLEN, Biol. Bull., 187, 309-18, 1994). This increase in fertility over the generations risks leading to the appearance in the longer or shorter term of a population of triploids whose fertility would be increasing, so that we run the risk of progressive sterilization of the environment, and of contamination of the stocks of autochthonous diploid oysters as a result of reproduction of triploid oysters, whose descendants are predominantly aneuploid.

2) The need to pass through triploids makes it particularly difficult and laborious to introduce, at the tetraploid level, any genetic progress normally and generally achieved at the diploid level. In fact, the diploid lines improved as a result of programs of genetic selection must first be used for producing triploids by classical methods of chemical induction. It is only later that the few triploids that are able to reach maturity and produce oocytes can be used as female parents in order to produce tetraploids.

It therefore seems particularly desirable to have a method of production of tetraploid oysters by which it is possible to pass directly from the diploid stage to the tetraploid stage without passing through the triploid stage.

The inventors put forward the hypothesis that the nonsurvival, beyond the larval stage, of the tetraploids produced on crossing diploid parents could have causes other than that the diploid oocyte is too small relative to the tetraploid nucleus, and that these causes might notably include a general decline in adaptive value (i.e. in the overall capacity for survival) resulting from the tetraploidy. This decline in adaptive value might be due to the expression of certain negative alleles that are normally suppressed in the diploids and the triploids but would not be suppressed, or would only be partially suppressed in the tetraploids.

This would result in low competitiveness of the tetraploid larvae, and therefore their rapid disappearance when they are bred mixed with diploid and triploid larvae, which are also present in the larval populations resulting from the crossing of diploid parents followed by retention of the first polar body.

Based on this hypothesis, the inventors posited that sorting of the larvae, in order to isolate the tetraploids and enable them to evade the very strong competition exerted by the diploid and triploid larvae, would make it possible to obtain viable tetraploids, starting from crossing involving only wild-type diploid parents.

They therefore developed a method based on the detection of tetraploid larvae, isolation of a larval subpopulation containing a high percentage of tetraploid larvae, and breeding of this subpopulation, these stages being repeated as many times as necessary in the course of development.

Thus, they found that the tetraploid larvae were characterized notably by slower development and therefore smaller size than the diploid and triploid larvae at the same stage of development. This observation confirms the hypothesis, formulated by the inventors, of the decline in adaptive value of the tetraploid larvae. In addition it makes it possible to simplify the sorting of the larvae for obtaining populations enriched in tetraploid larvae, since this sorting can be carried out on the basis of larval size.

The present invention therefore relates to a method of producing tetraploid bivalves, characterized in that it comprises:

a) fertilization of oocytes from diploid females by sperm from diploid males, followed by the induction of retention of the first polar body of the fertilized eggs;

b) culture of the larvae obtained after said fertilization;

c) isolation, from the population of larvae cultivated in stage b), of a subpopulation enriched in tetraploids, comprising at least 20%, preferably at least 30%, of tetraploid larvae;

d) culture of the subpopulation of larvae isolated in stage c).

Retention of the first polar body can be induced, classically, by any treatment that induces inhibition of assembly of the microtubules, generally carried out between the fifth and the twenty-fifth minute postfertilization, the duration of which can vary from 10 to 20 minutes. It can for example be treatment with a chemical agent, such as colchicine, caffeine, nocodazole, cytochalasin B, or 6-DMAP, or a physical treatment such as moderate thermal shock or hyperbaric shock.

According to a preferred embodiment of the present invention, retention of the first polar body is induced by treatment with cytochalasin B. The treatment with cytochalasin B can be carried out between the 5th and the 25th minute after fertilization, for 10 to 20 minutes. Preferably it is carried out starting from the 10th minute after fertilization, for about 15 minutes. Particularly advantageously, cytochalasin B is used at a final concentration per liter of treatment medium between 0.3 and 0.7 mg, preferably of the order of 0.5 mg. These concentrations, which are half as strong as those usually employed for the induction of retention of the first polar body in the production of triploid oysters, make it possible to limit the toxic effect of cytochalasin B, but without diminishing the effectiveness of induction.

It is also possible to use, instead of cytochalasin B, some other chemical agent, such as colchicine, caffeine, nocodazole, or 6-DMAP (300 to 500 µm), or a physical treatment such as moderate thermal shock (30 to 40° C.) or hyperbaric shock. For each of these treatments, the conditions selected will preferably be more moderate than when the same treatment is employed for inducing the retention of the first polar body in the production of triploid oysters.

Particularly advantageously, the method according to the invention comprises the following additional stages:

e) isolation, from the subpopulation of larvae cultivated in the preceding stage, of a subpopulation rich in tetraploids comprising at least 20%, advantageously at least 30%, of tetraploid larvae;

f) culture of the subpopulation of larvae isolated in stage e).

Generally, the cultivation in stage b) is carried out for 6 to 10 days, preferably for about 8 days, and the cultivation in stages d) and f) is carried out for 2 to 3 days.

These stages of isolation of a subpopulation rich in tetraploids and cultivation of the subpopulation isolated can be repeated several times, until the larvae reach the pediveliger stage (size between 220 and 250 µm). Advantageously they are repeated at least 3 times, preferably at least 4 times, at intervals of 2 to 3 days.

According to a particularly preferred embodiment of the method according to the invention, the sorting of the larvae to isolate a subpopulation enriched in tetraploids is carried out on the basis of their size.

In fact, as stated above, the tetraploid larvae are smaller than the diploid and triploid larvae at the same stage of development. Generally, the average size of the tetraploid larvae is 20 to 30% less than that of the diploid larvae, and 25 to 35% less than that of the triploid larvae of the same species at the same stage of development, and cultivated in the same conditions.

This means that the larvae can be sorted easily, simply by passing through a sieve of appropriate mesh, selected in relation to the species in question, the stage of larval development, and the cultivation conditions.

Advantageously, additional stages of isolation of a subpopulation enriched in tetraploids and cultivation of the subpopulation isolated can be carried out after the pediveliger stage, on the settled spats. Starting from this stage, they will preferably be repeated at longer intervals than previously, for example every 8 to 15 days.

In this case, to carry out sorting by sieving, the attachment substrate supplied for the pediveliger larvae is constituted of particles of size roughly equal to that of the larvae during settlement, allowing attachment of a single larva per particle. The substrate used can notably be microsplinter particles, obtained by grinding oyster shells.

After each stage of isolation of a subpopulation, the percentage of tetraploids in the subpopulation selected can, if required, be verified by conventional methods of determination of the level of ploidy. We can for example use flow cytometry, on a sample of at least 100 individuals, taken from said subpopulation.

The method according to the invention can be used for all species of bivalves (for example Pectinidae (scallops), mussels (*Mytilus edulis* and *Mytilus galloprovincialis*), clams, etc.) for which we wish to produce tetraploids (notably with a view to using them for the production of triploids). It is quite particularly interesting for the production of tetraploid oysters, and can for example be used not only for oysters of the species *Crassostrea gigas*, as illustrated in the examples given below, but also for any other species of the genus *Crassostrea* (notably *Crassostrea virginica*), *Saccostrea* (for example *Saccostrea commercialis*), or in species of the genus *Ostrea*, such as *Ostrea edulis*.

The method according to the invention makes it possible to obtain viable tetraploid bivalves, and notably oysters, starting from any diploid parents. In particular, it does not require any selection of the female parents with respect to the size of their oocytes.

It makes it possible to produce tetraploid parents, directly from diploid wild-type parents—without passing through a triploid stage. These tetraploid parents can then be used for the production of triploids without running the risks, mentioned above, connected with increase in fertility of the triploids over the generations.

The method according to the invention also makes it possible to introduce, directly in tetraploids, genetic improvements obtained in diploids. For this, it is sufficient to use, as starting material for application of this method, oocytes and sperm obtained from animals of a selected diploid line. The tetraploids obtained can then be used for the production of triploids that also incorporate the same improvement.

The present invention will be better understood from the supplementary description that follows, referring to examples illustrating the application of the present invention for the production of viable tetraploid oysters.

EXAMPLE 1

Figure 1:
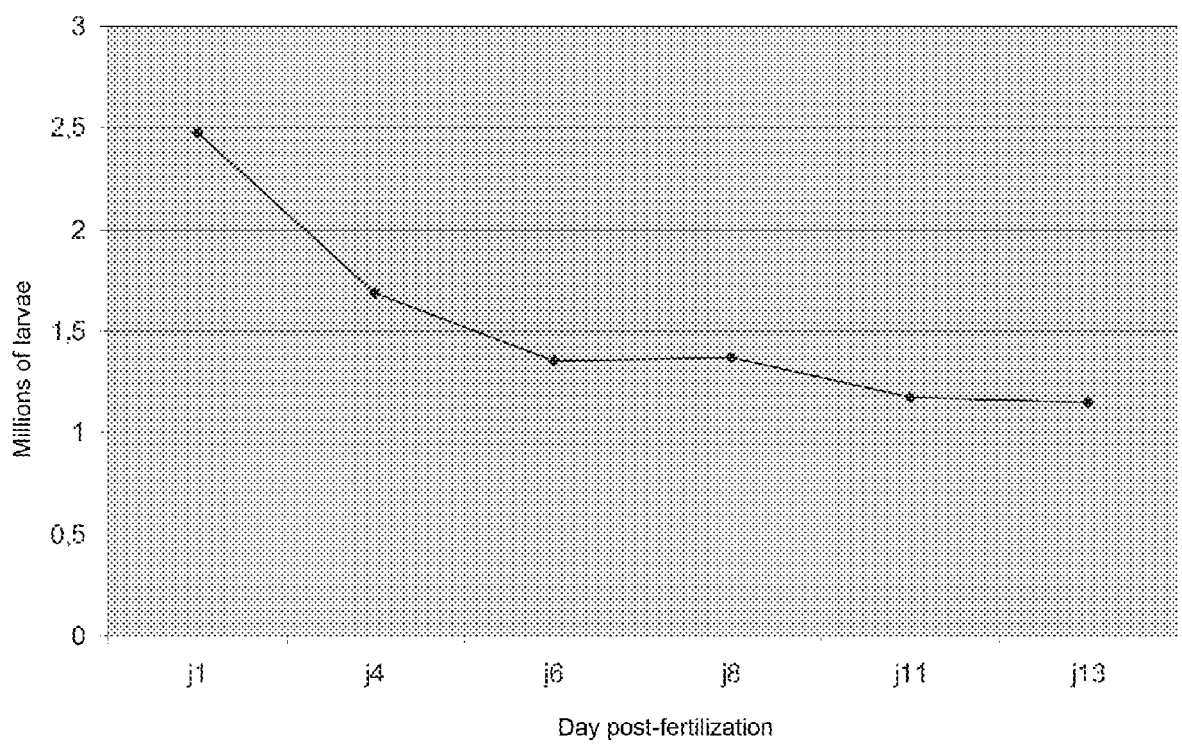
FIG. 1 shows monitoring the survival rate during the first days of breeding shows a definite decrease in survival of the larvae between D1 and D6 post-fertilization.

Induction of Polyploidy and Breeding of Larvae

The diploid parents used for the experiments are from a natural collection area of wild-type diploid spat in the Marennes Oléron Bay. Six female parents and four male parents were used for collecting gametes by scarification of the gonads. 15 million oocytes and 3 billion spermatozoids obtained from the ten parents were used for carrying out crossing in 1 L of filtered seawater at 25° C. Retention of the first polar body was effected using cytochalasin B (CB), dissolved in DMSO, to a final concentration of 0.5 mg/l. CB was applied for 15 minutes, starting from the tenth minute after fertilization.

This protocol for induction of polyploidy is similar to those already published in the literature for the production of triploids (GUO et al., Biol. Bull., 183, 381-93, 1992; GÉRARD et al., Aquaculture, 174, 229-42 1999). However, the final concentration of CB was reduced (0.5 mg/l instead of 1 mg/l), in order to limit the toxic effect of this product, though without reducing the degree of induction of polyploidy.

The CB is then removed after sieving the embryos through a nylon filter of 10 μm mesh and washing for 15 minutes in filtered seawater containing 0.1% DMSO.

As a control, 15 million oocytes and 5 billion spermatozoids obtained from the same parents were used for carrying out crossing in the same conditions, except for the treatment with CB.

Then the embryos from each of the two groups (control group and group treated with CB) were returned to culture in cylindrical-conical tanks containing 150 L of filtered seawater at 22° C. and aerated by a bubbler incorporated in the breeding tank.

So as to be able to estimate the rate of hatching and possible mortality of the larvae, the latter are sieved after 24 hours post-fertilization, through a 45 μm diameter filter, collected in a graduated cylinder containing 1 or 2 L of filtered seawater, and the total number of larvae is estimated from a count in a 50 μl sample.

In addition, the ploidy of the larvae is determined by flow cytometry. After each sieving, a sample of larvae (at least 100 larvae) is taken and put in a 1.5 ml tube. After removal of the seawater by brief centrifugation, the larvae are taken up in 1 ml of lysis buffer (5 mM $MgCl_2$, 85 mM NaCl, 10 mM Tris, 0.1% Triton X-100, pH7). Then the larvae are ground by means of a plastic plunger and the nuclei released are filtered through a nylon filter of 30 μm mesh (Partec Celltrics) and collected in a cytometry analysis tube, then labeled with DAPI (4',6-diamidino-2-phenylindole dihydrochloride) at a final concentration of 1 μg/ml, by adding 1 ml of lysis buffer containing DAPI at 2 μg/ml and 2 μl of internal control of ploidy (trout erythrocytes, TRBC, Coulter DNA Reference Calibrator, 629972).

After a minimum incubation time of 30 min on ice and in the dark, the cytometric analyses are performed using a Partec PAII cytometer. Each analysis (channel FL4, linear scale of 1024 channels) is carried out on a minimum of 2000 particles. The results obtained are presented in the form of frequency histograms with a Gaussian distribution of the events within each peak. The peaks are recorded as "peak x" when they were identified automatically by the FloMax™ software, or "RN/PK x" when they were identified manually by the operator (x being the number of the peak).

In the group treated with CB, the proportion of larvae D on D1 is estimated at 16.5% (versus 42% for the untreated control), which represents a population of larvae D of approx. 2.5 million larvae.

Starting from the second day post-fertilization, the water is renewed every other day after sieving. Up to D6 post-fertilization, the larvae were sieved through a filter of 45 μm. At each renewal, the larvae are counted and their level of ploidy is determined by flow cytometry, as described above.

Then the larvae are returned to their respective cylindrical-conical breeding tanks observing a maximum density of 10 000 larvae/L on D4 post-fertilization and of 6500 larvae/L on D6 post-fertilization.

The larvae are fed every day with a mixture of food algae cultivated in the laboratory and containing 70% of *Isochrysis galbana*, Tahiti strain, and 30% of *Chaetoceros gracilis* at a concentration of 25 cells/μl/day.

Monitoring the survival rate during the first days of breeding shows a definite decrease in survival of the larvae between D1 and D6 post-fertilization (FIG. 1). This decrease can be explained both by the harmful effect of the treatment with CB and especially by the effect of the high density of larvae in the breeding tank.

Figure 2:
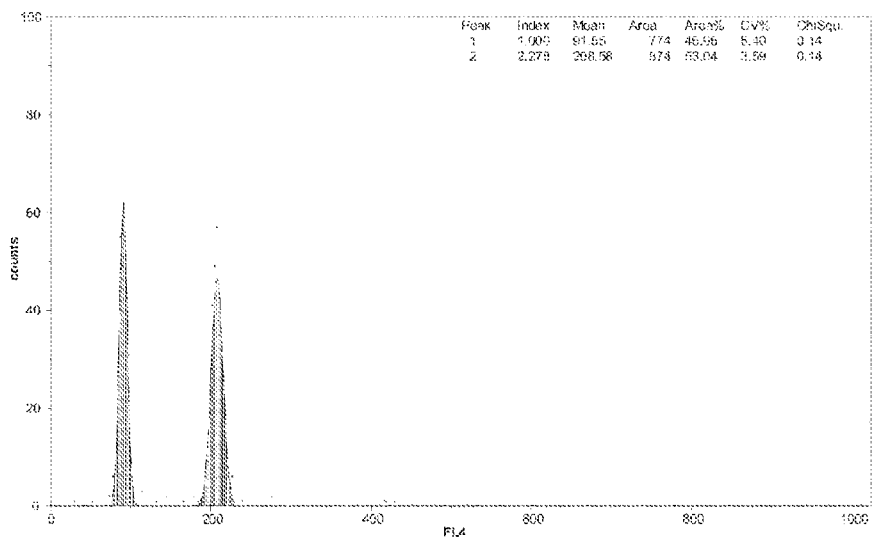
FIG. 2 shows that the control crossing has a population of exclusively diploid nuclei.
Figure 3:
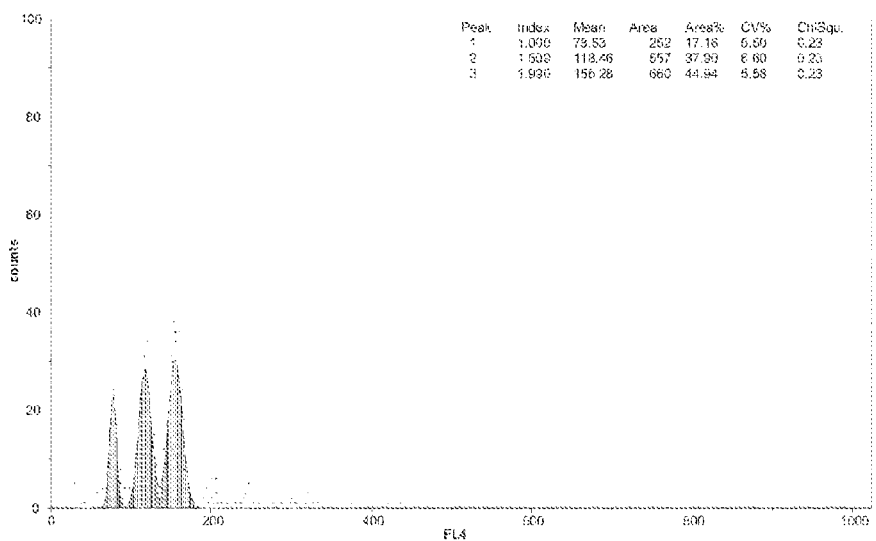
FIGS. 3 and 4 show the samples of larvae obtained from induction of retention of GPI that shows three types of nuclear populations corresponding to the following levels of ploidy: diploid (around 20% on average, peak 1), triploid (around 40% on average, peak 2) and tetraploid (around 40% on average, peak 3).
Figure 4:
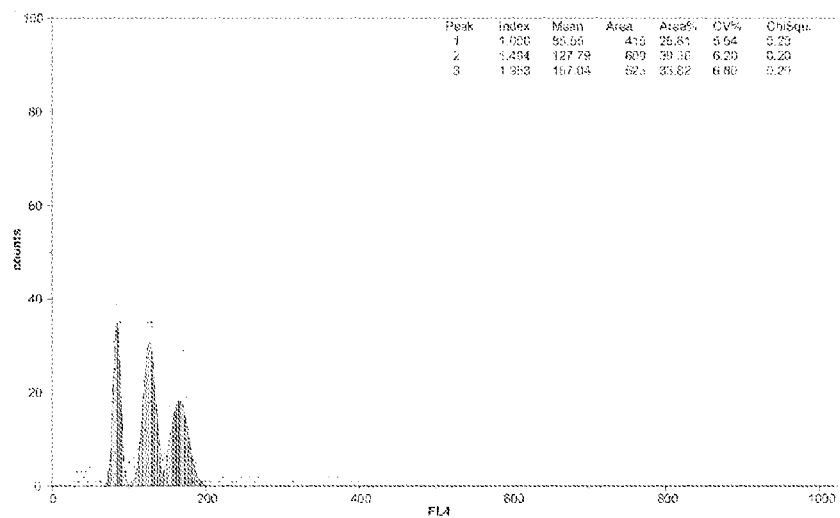

Between D1 and D6 post-fertilization, the cytometric analyses with untreated larvae and larvae treated with CB show that:

The control crossing has a population of exclusively diploid nuclei (FIG. 2, "peak 1"), The samples of larvae obtained from induction of retention of GPI show (FIGS. 3 and 4) three types of nuclear populations corresponding to the following levels of ploidy: diploid (around 20% on average, "peak 1"), triploid (around 40% on average, "peak 2") and tetraploid (around 40% on average, "peak 3").

After D6 post-fertilization, the population of larvae stabilizes and the breeding of larvae continues without notable mortality until settlement of the larvae.

The sievings are carried out in the morning and every two or three days. Up to the sixth day postfertilization, the larvae were sieved, nonselectively, through a sieve of 45 μm.

Next, selective sievings were carried out, adapting the sieve size to the target population of larvae, and different populations of larvae were constituted, based on their rate of growth (estimated from the different sizes of sieves), and their levels of ploidy (verified by flow cytometry).

In this way, populations with strong development called "head of batch", with medium development called "body of batch" and with slow development called "tail of batch" were constituted as a function of these two criteria, and were kept in separate tanks. The ultimate aim of this method of selective sorting as a function of size and ploidy is to be most favorable for the growth and survival of the tetraploid larvae, by maximizing, within the different parts of the breeding batch, their proportion relative to the diploid and triploid larvae.

Thus, on D8 post-fertilization, the first sieving selective for the size of the larvae was carried out and two populations of larvae were bred separately: the population "head of batch I" having normal growth and minimum size of 80 µm and a population "tail of batch I" with slower growth, and size between 65 µm and 80 µm.

The following sievings were carried out on D11, D13, D15, D18, D20, D23, D25, D27, and D29 post-fertilization.

Figure 5:
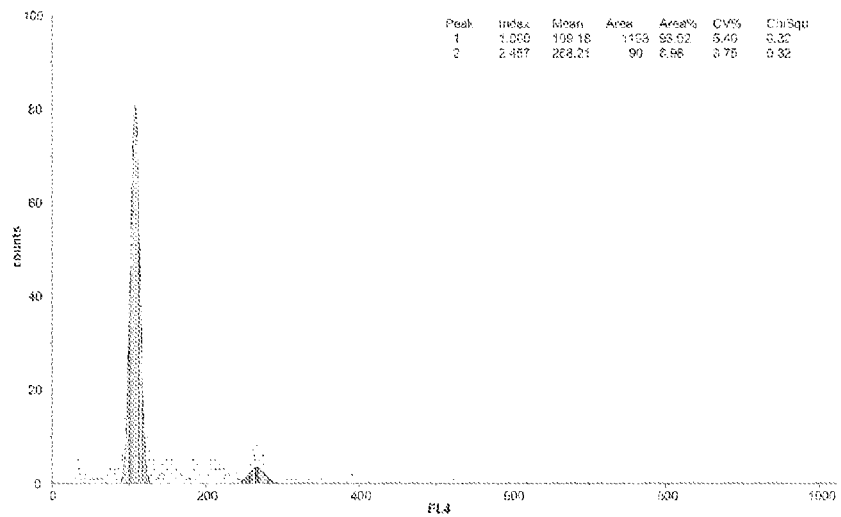
FIG. 5 shows that the control crossing still has an exclusively diploid population of nuclei (peak 1, with peak 2 corresponding to the internal control TRBC).
Figure 6:
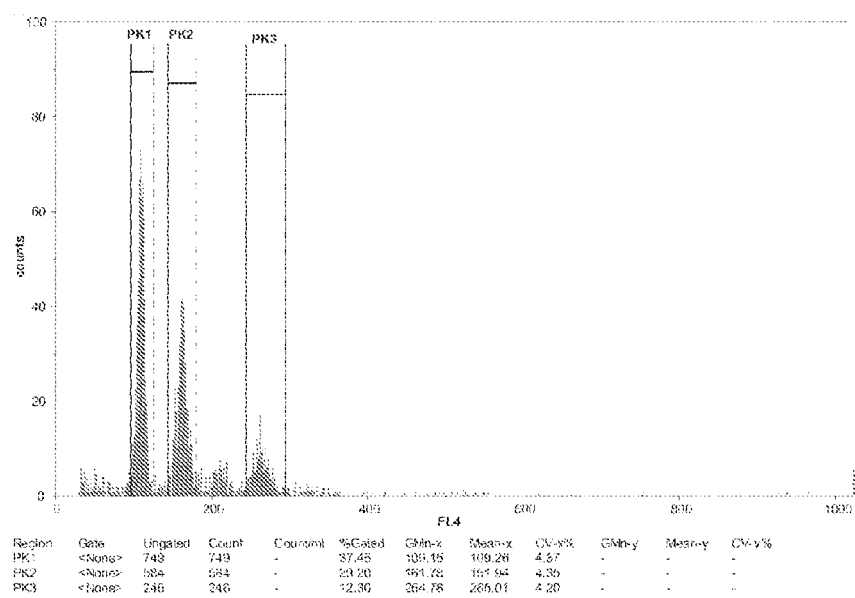
FIG. 6 shows that no proportion of tetraploid larvae was detected (the peak PK 3 corresponding to the internal control TRBC).

On D11 post-fertilization, the cytometric analyses performed on the control group, as well as on the two populations of larvae treated with CB show that:

The control crossing still has an exclusively diploid population of nuclei (FIG. 5, "peak 1", with the peak "peak 2" corresponding to the internal control TRBC), The samples of treated larvae obtained from the population "head of batch I" having a minimum size of 80 µm (T≧80 µm) show that this population is constituted solely of diploid larvae (at 57%, "PK1") and of triploid larvae (at 43%, "PK 2"). No proportion of tetraploid larvae was detected there (FIG. 6, the peak "PK 3" corresponding to the internal control TRBC).

Figure 7:
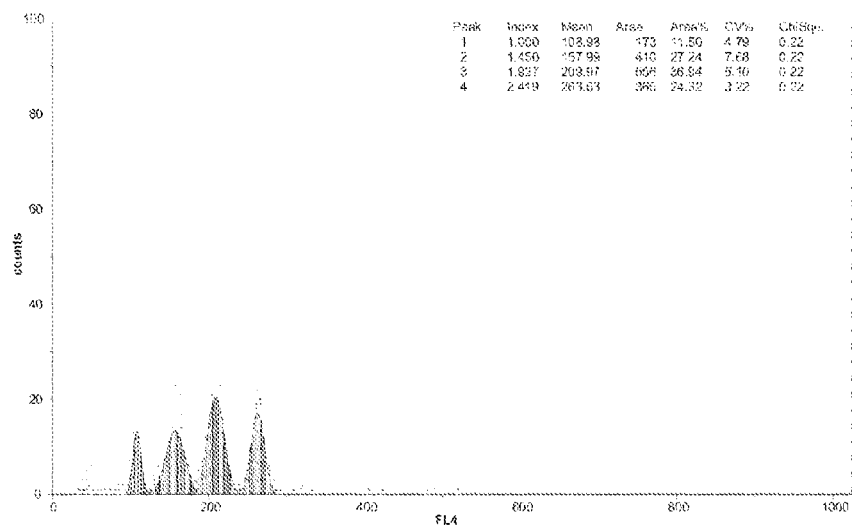
FIG. 7 shows the cytometric analyses that show the population is constituted of 15% of diploid larvae (peak 1), 40% of triploid larvae (peak 2) and especially 45% of tetraploid larvae (peak 3), where peak 4 corresponds to the internal control TRBC.

The samples of treated larvae obtained from the population "tail of batch I" having a size less than 80 µm (65 µm<T<80 µm) show that this population has a radically different constitution, whether in terms of classes of ploidy or in terms of proportion of these classes of ploidy. The cytometric analyses show that this population is constituted of 15% of diploid larvae (peak 1), 40% of triploid larvae (peak 2) and especially 45% of tetraploid larvae (peak 3) (FIG. 7 where the peak "peak 4" corresponds to the internal control TRBC).

This result shows that the tetraploid fraction of the total population of larvae being bred is confined to the part "tail of batch" in the breeding of larvae, thus confirming our hypothesis according to which there is a differential development of the larvae having different levels of ploidy when they are bred mixed together. Thus, the tetraploid level of ploidy is shown to be that which gives the lowest growth rate when it is in competition with the diploid and triploid levels.

Following breeding, particular attention was paid to the population "tail of batch I", the only one containing tetraploids, and two selective sievings were performed on said "tail of batch I" population so as to be able to isolate two subpopulations increasingly rich in tetraploid larvae, namely after sieving through 60 and 80 µm sieves.

Thus, the first subpopulation (called "tail of batch I") is constituted of the larvae whose size is greater than 65 µm, and less than 80 µm, whereas the second subpopulation (called "body of batch I") is constituted of the larvae whose size is greater than or equal to 80 µm, and is generally up to 100 µm.

Figure 8:
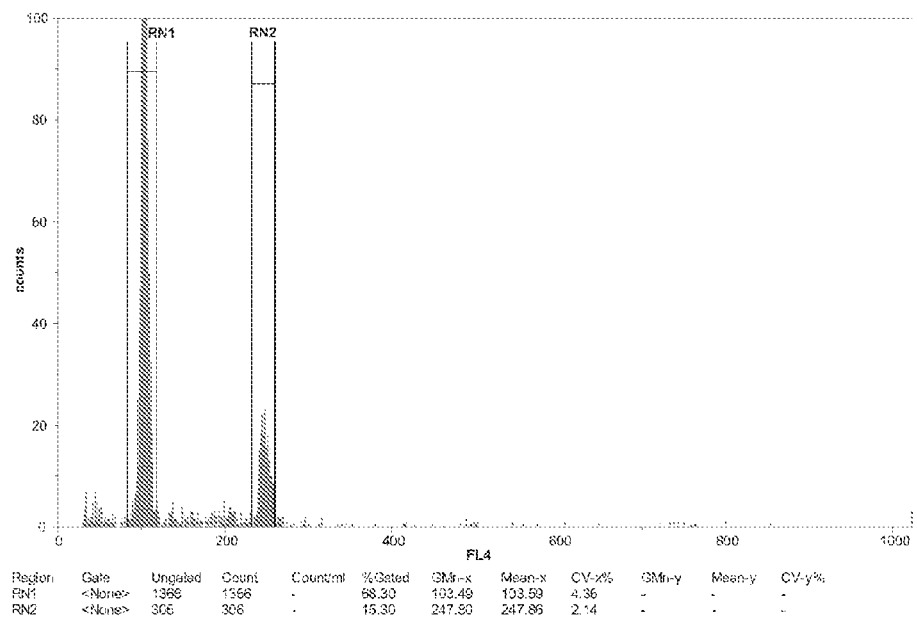
FIG. 8 shows that the untreated control still only shows exclusively diploid nuclei (peak RN 1, peak RN 2 corresponding to the internal control TRBC).

On D13 post-fertilization, the cytometric analyses performed on untreated larvae or larvae treated with CB show that:

The untreated control still only shows exclusively diploid nuclei (peak "RN 1" in FIG. 8, the peak "RN 2" corresponding to the internal control TRBC).

Figure 9:
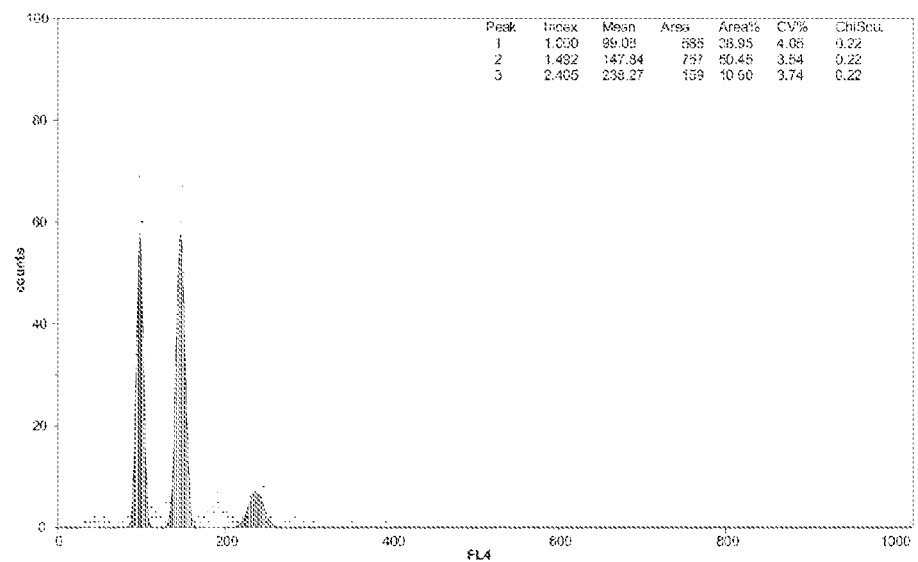
FIG. 9 shows that the population of treated larvae in head of batch I continues to be exclusively constituted of diploid larvae (45%, peak1) and triploid larvae (55%, peak 2), where peak 3 corresponds to the internal control TRBC.

The population of treated larvae "head of batch I" continues to be exclusively constituted of diploid larvae (45%, peak1) and triploid larvae (55%, peak2), (FIG. 9 where "peak3" corresponds to the internal control TRBC). This population is composed of larvae displaying normal growth and that have reached a minimum size of 100 µm.

Figure 10:
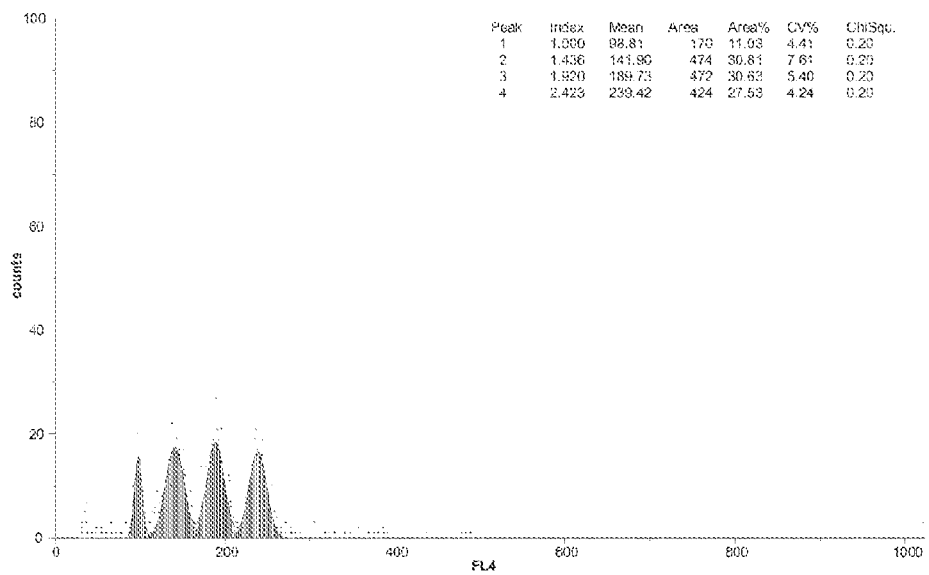
FIG. 10 shows that the populations of treated larvae in body of batch I and tail of batch I are the only two still showing a high proportion of tetraploid larvae (40 to 50% represented by the peak 3, the peaks 1-2-4 corresponding respectively to the diploid, triploid nuclei and internal control TRBC.
Figure 11:
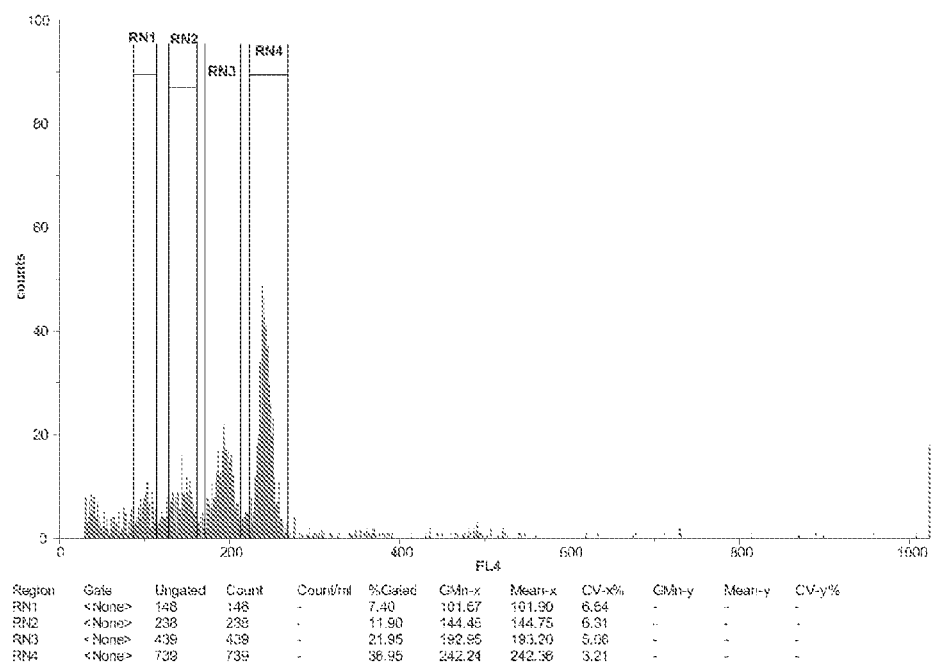
FIG. 11 shows that the populations of treated larvae in body of batch I and tail of batch I are the only two still showing a high proportion of tetraploid larvae (40 to 50% represented by the RN 3, RN 1-2-4 corresponding respectively to the diploid, triploid nuclei and internal control TRBC.

The populations of treated larvae "body of batch I" and "tail of batch I" are the only two still showing a high proportion of tetraploid larvae (40 to 50% represented by the peaks "peak 3" in FIG. 10 and "RN 3" in FIG. 11). The peaks "peak 1-2-4" and "RN 1-2-4" correspond respectively to the diploid, triploid nuclei and internal control TRBC of FIGS. 10 and 11).

On D15 post-fertilization, our efforts were focused on the conditions of breeding of the populations "body of batch I" and "tail of batch I" of the treated larvae (those containing tetraploids). Selective sievings are performed on these populations, using sieves of mesh 65, 100 and 125 µm, in order to constitute new subpopulations:

with strong growth called "head of batch II" with size between 125 and 150 µm;

with medium growth called "body of batch II" with size between 100 and 125 µm;

with weak growth called "tail of batch II" with size between 65 and 100 µm.

Figure 12:
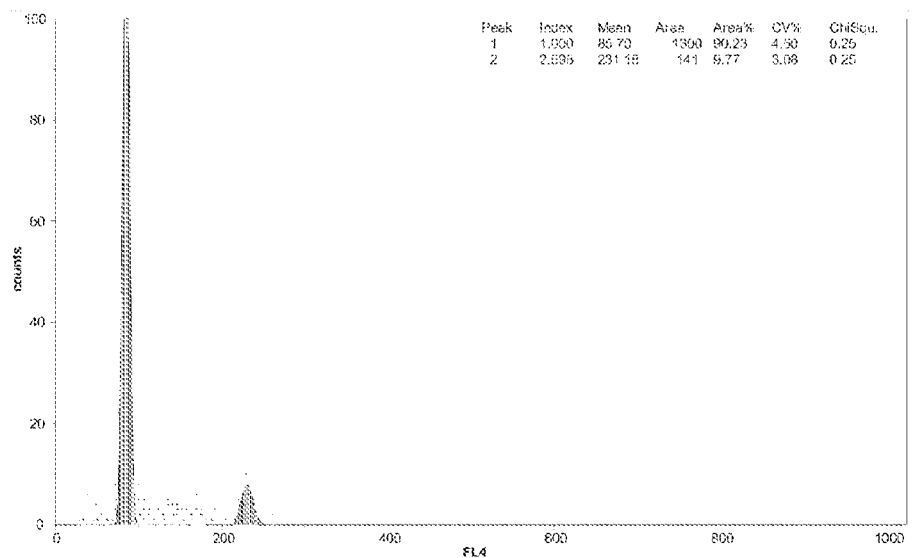
FIG. 12 shows that the untreated control still only shows exclusively diploid nuclei (peak 1, peak 2 corresponds to the internal control TRBC).

Cytometric analyses carried out with untreated larvae and larvae treated with CB show that:

The untreated control still only shows exclusively diploid nuclei ("peak1", FIG. 12; "peak 2" corresponds to the internal control TRBC).

The population of treated larvae "head of batch I" is still constituted exclusively of diploid larvae (at a level of 45%) and triploid larvae (at a level of 55%).

Figure 13:
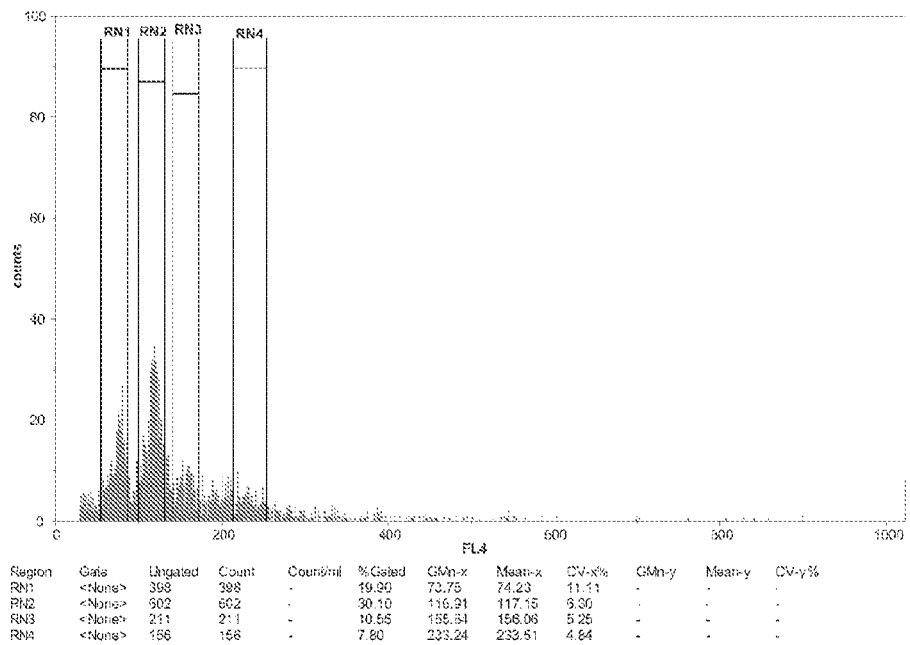
FIG. 13 shows that the proportion of tetraploid larvae is lowest (15%) in the head of batch II (peak RN3).
Figure 14:
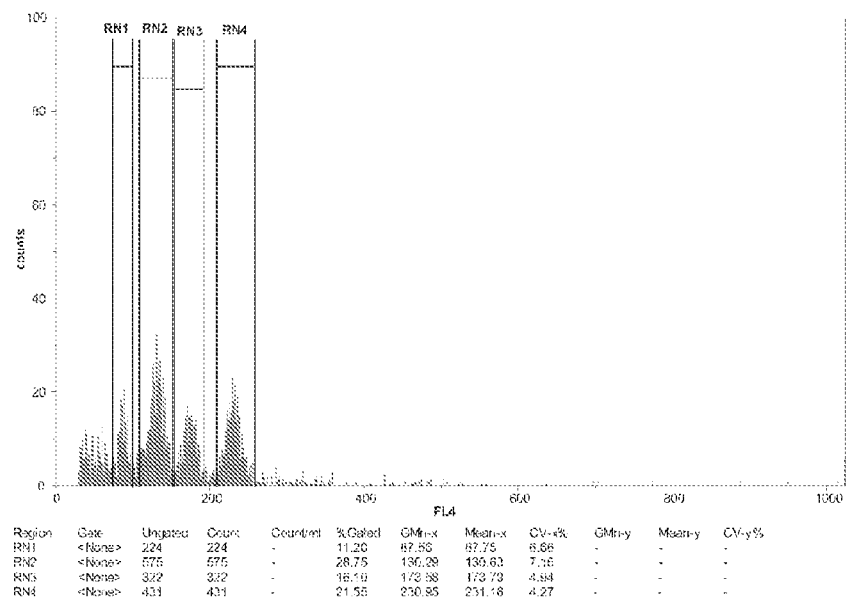
FIG. 14 shows that in the part of body of batch II, the proportion of tetraploid larvae has an intermediate value (28%, peak RN3).
Figure 15:
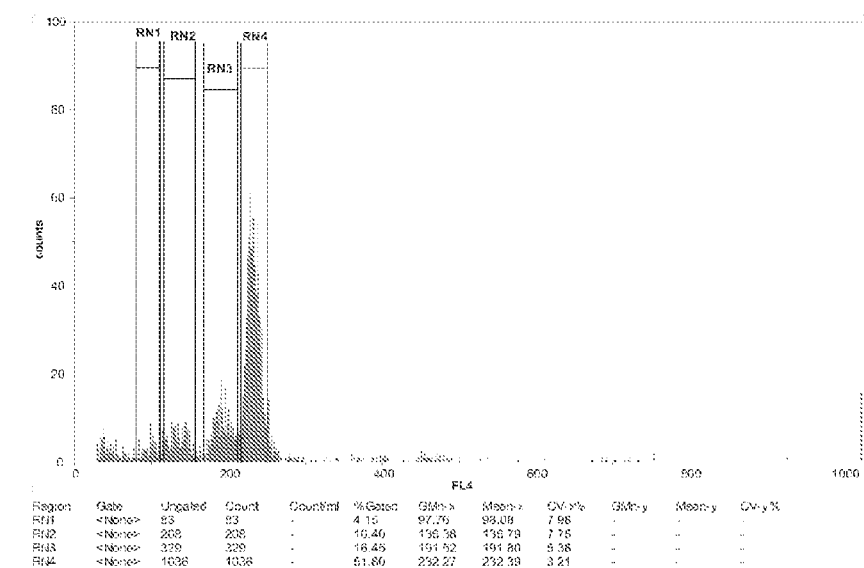
FIG. 15 shows that the proportion of tetraploid larvae is highest (50%) in the tail of batch II (peak RN3).

The populations of larvae treated with CB "head of batch II" (150 µm>T≧125 µm), "body of batch II" (125 µm>T≧100 µm) and "tail of batch II" (100 µm>T≧65 µm) continue to show a notable proportion of tetraploid larvae (FIGS. 13, 14, 15 where the peaks "RN 1-2-3-4" correspond respectively to the diploid, triploid, tetraploid nuclei, and internal control TRBC). However, the size of this tetraploid population is very different from one part of the breeding batch to another. The proportion of tetraploid larvae is lowest (15%) in the "head of batch II" (FIG. 13, peak "RN3"), and highest (50%) in the "tail of batch II" (FIG. 15, peak "RN3"). In the part "body of batch II", the proportion of tetraploid larvae has an intermediate value (28%, FIG. 14, peak "RN3"). It is therefore clear that the breeding batches with the greatest amount of tetraploid larvae are those which cross the least quickly, which emphasizes once again the difference in general value of adaptation of the three levels of ploidy and the need to carry out selective sorting to maintain the tetraploid larvae.

Figure 16:
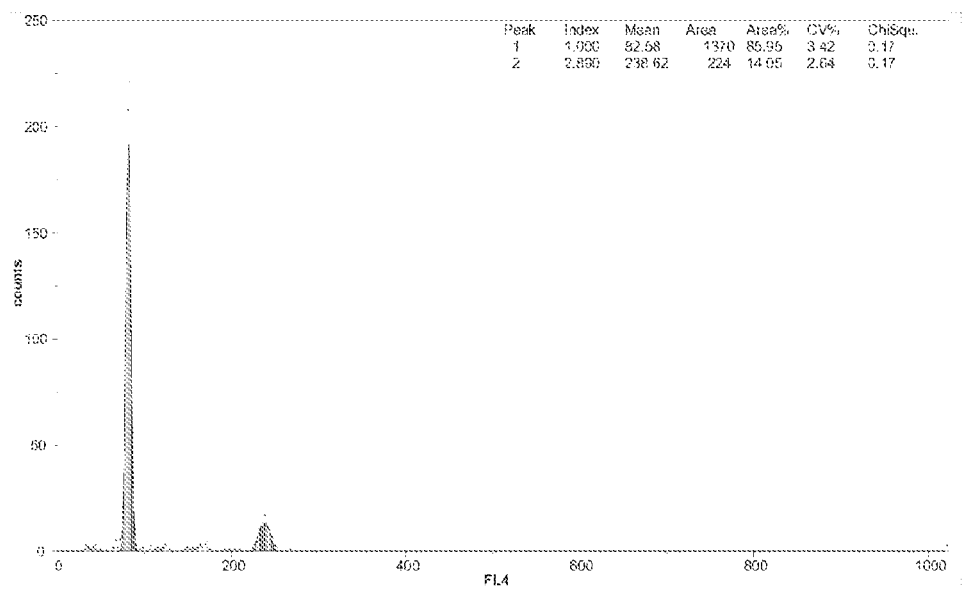
FIG. 16 shows that the cytometric analyses performed on D18 continue to show an exclusively diploid level in the control (peak 1; peak 2 corresponds to the internal control TRBC).
Figure 17:
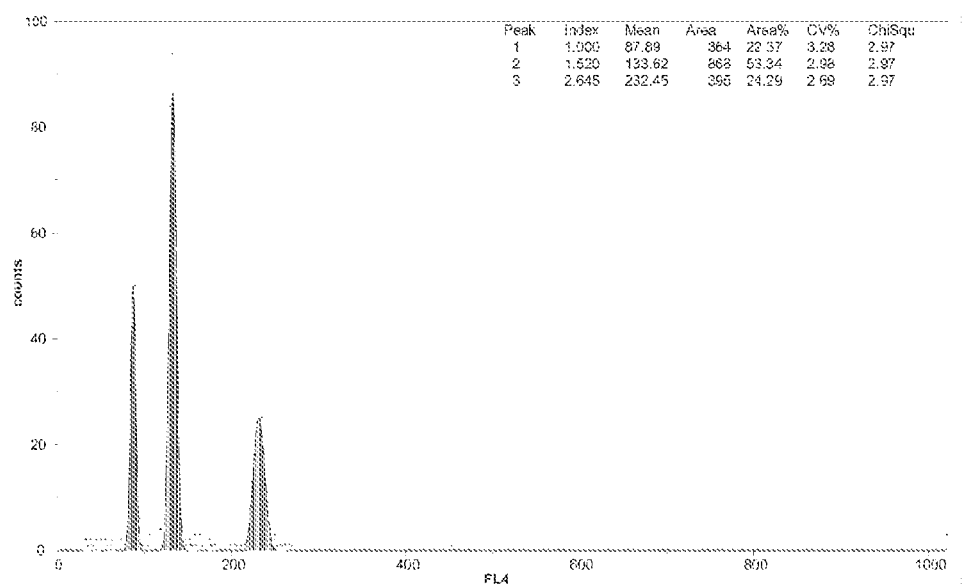
FIG. 17 shows a mixture of diploids (at 30%, peak 1) and triploids (at 70%, peak 2) in the population of head of batch I (peak 3 corresponds to the internal control TRBC).

On D18 post-fertilization, some of the treated larvae in the population "head of batch I" (T≧250 µm) are pediveligers and are beginning to settle, two days before the untreated control larvae. The cytometric analyses performed on D18 continue to show an exclusively diploid level in the control (FIG. 16, "peak1"; "peak2" corresponds to the internal control TRBC), and a mixture of diploids (at 30%, "peak1") and triploids (at 70%, "peak2") in the population "head of batch I" (FIG. 17 where "peak 3" corresponds to the internal control TRBC).

Figure 18:
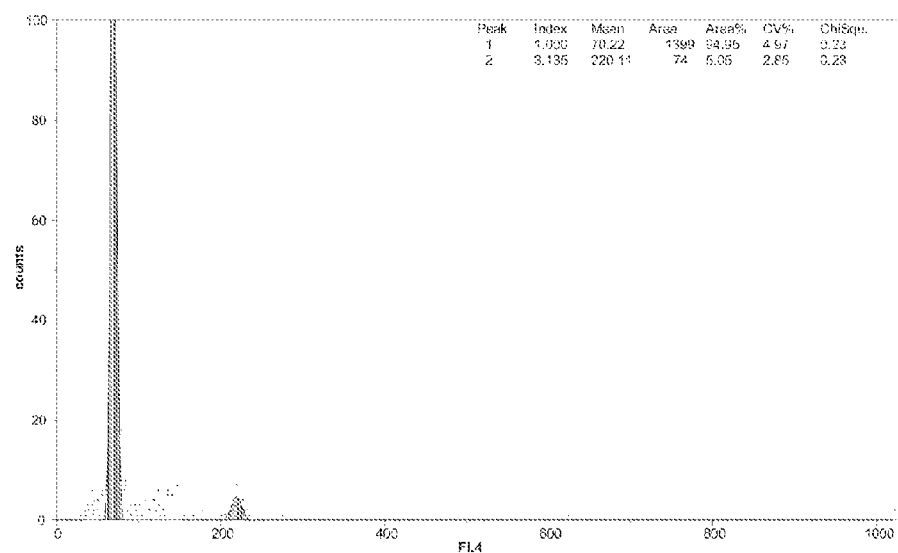
FIG. 18 shows that the untreated control continues to show an exclusively diploid level (peak 1).
Figure 19:
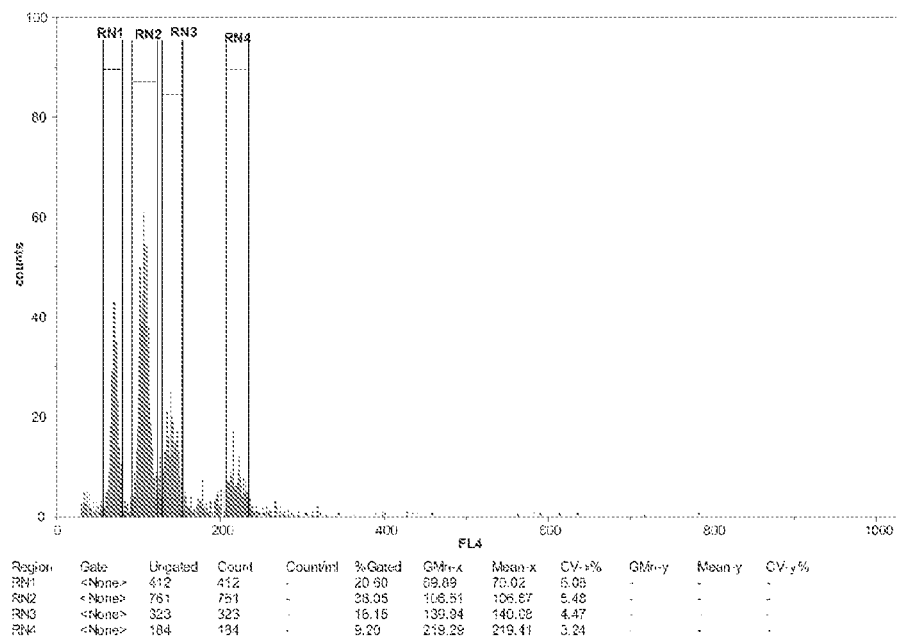
FIG. 19 shows that head of batch II (T≧180 μm) shows roughly the same proportions of tetraploid larvae as on D15 post-fertilization (20% of tetraploids represented by the peak RN3).
Figure 20:
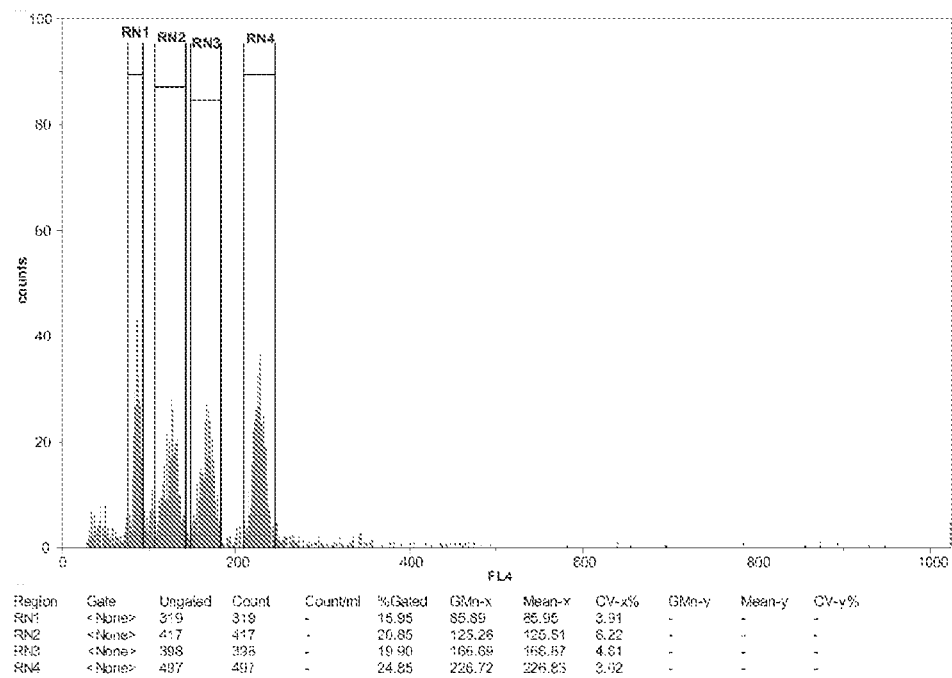
FIG. 20 shows that body of batch II (180 μm>T≧150 μm) shows roughly the same proportions of tetraploid larvae as on D15 post-fertilization (35% of tetraploids represented by the peak RN3).
Figure 21:
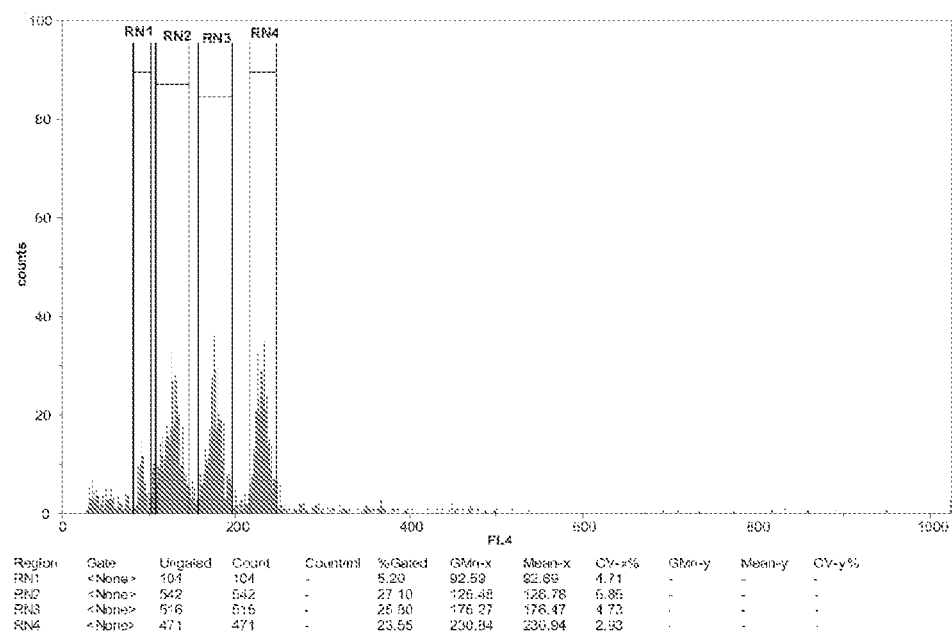
FIG. 21 shows that tail of batch II (150 μm>T≧100 μm)) shows roughly the same proportions of tetraploid larvae as on D15 post-fertilization (45% of tetraploids represented by the peaks RN3).
Figure 22:
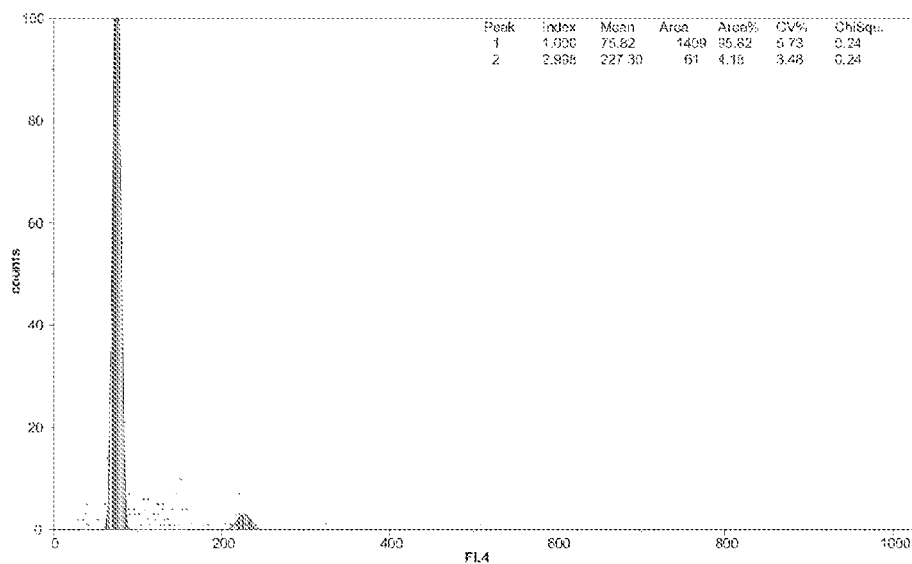
FIG. 22 shows that the untreated control continues to show an exclusively diploid level (peak 1).
Figure 23:
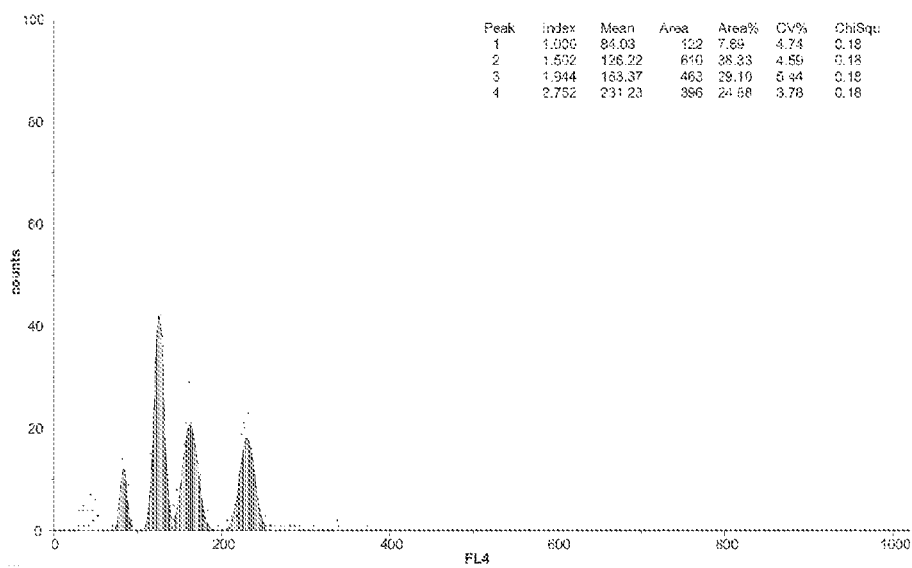
FIG. 23 shows that head of batch II (T≧180 μm) shows roughly the same proportions of tetraploid larvae as on D15 post-fertilization (20% of tetraploids represented by peak 3)
Figure 24:
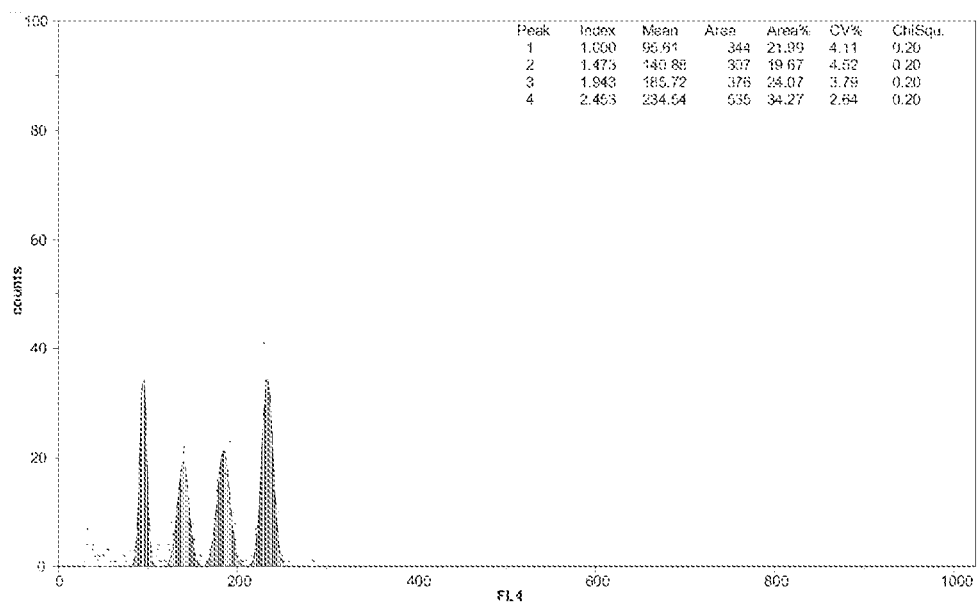
FIG. 24 shows that body of batch II (180 μm>T≧150 μm) shows roughly the same proportions of tetraploid larvae as on D15 post-fertilization (35% of tetraploids represented by peak 3).
Figure 25:
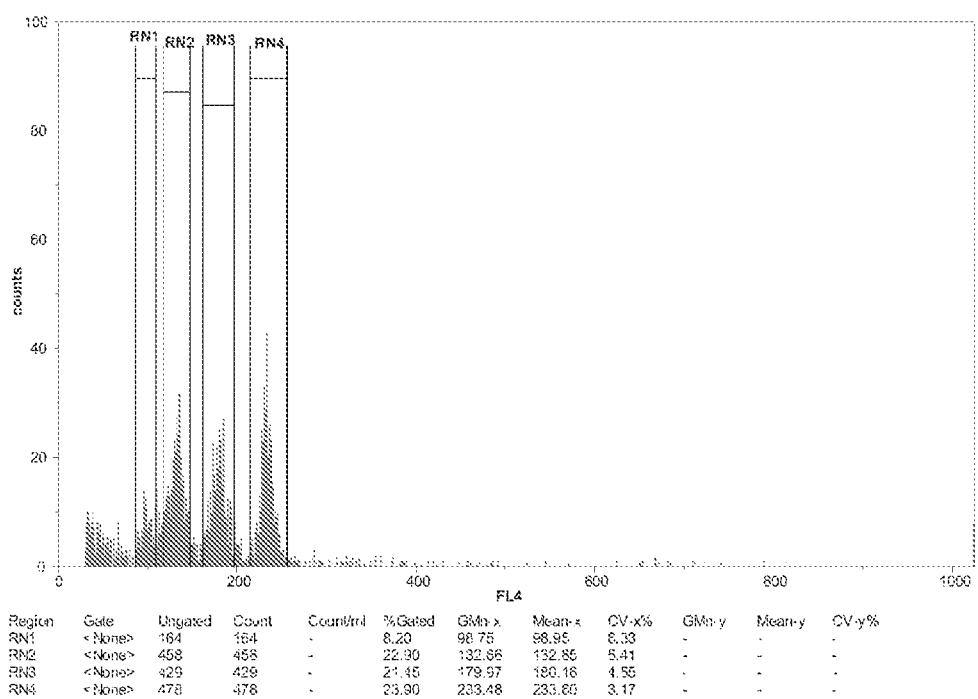
FIG. 25 shows that tail of batch II (150 μm>T≧100 μm)) shows roughly the same proportions of tetraploid larvae as on D15 post-fertilization (45% of tetraploids represented by peak 3).

On D20 and D23 post-fertilization, whereas the untreated control continues to show an exclusively diploid level (FIGS. 18 and 22, "peak1"), the breeding batches containing tetraploid larvae (head of batch II (T≧180 µm); body of batch II (180 µm>T≧150 µm) and tail of batch II (150 µm>T≧100 µm)) show roughly the same proportions of tetraploid larvae as on D15 post-fertilization (respectively 20, 35 and 45% of tetraploids represented by the peaks "RN/peak 3" in FIGS. 19-21 and 23-25, where the other peaks "peak/RN 1-2-4" correspond respectively to the diploids, triploids, and internal control TRBC). Moreover, even if their growth seems manifestly slower than that of the untreated control, these larvae have despite everything shown an increase in their minimum size (respective minimum sizes of 180, 150 and 100 μm on D23 versus 125, 100 and 65 μm on D15 post-fertilization).

Figure 26:
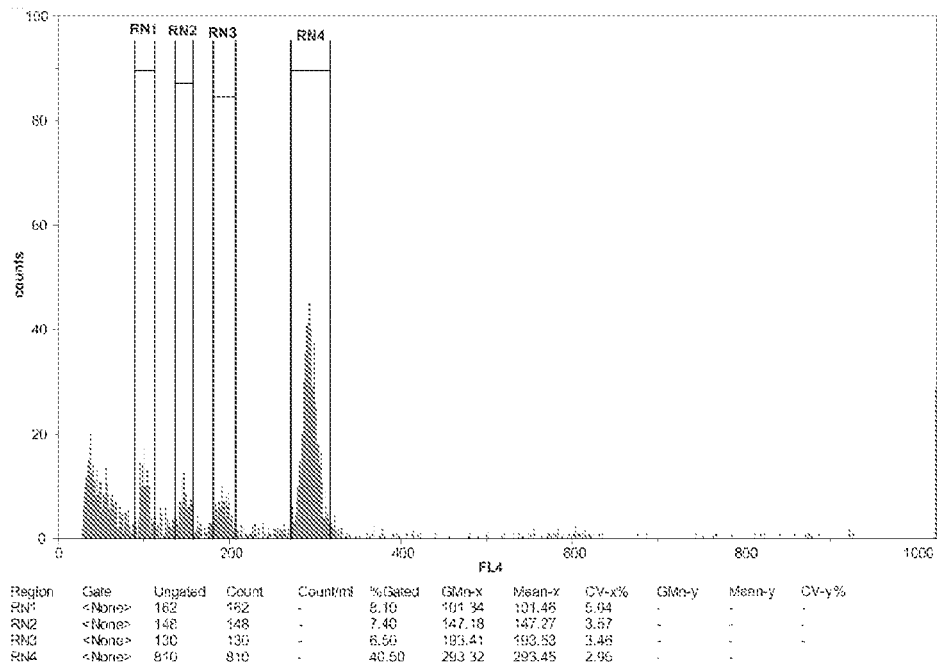
FIG. 26 shows that on D25 post-fertilization, a first cohort of pediveliger larvae (T≧250 μm) containing 30% of tetraploid larvae (peak RN3, the other peaks RN 1-2-4 corresponding respectively to the diploids, triploids, and to the internal control TRBC).
Figure 27:
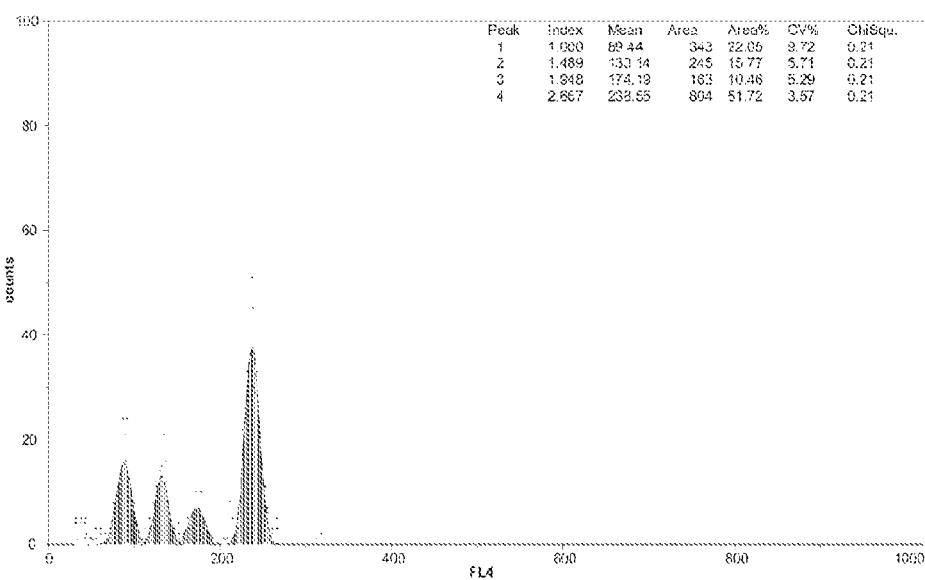
FIGS. 27, 28 and 29 show that on D27 and D29, three settlements of pediveliger larvae containing variable proportions of tetraploid larvae ranging from 20 to 40% (peak 3; the other peaks 1-2-4 corresponding respectively to the diploid and triploid nuclei, and internal control TRBC).
Figure 28:
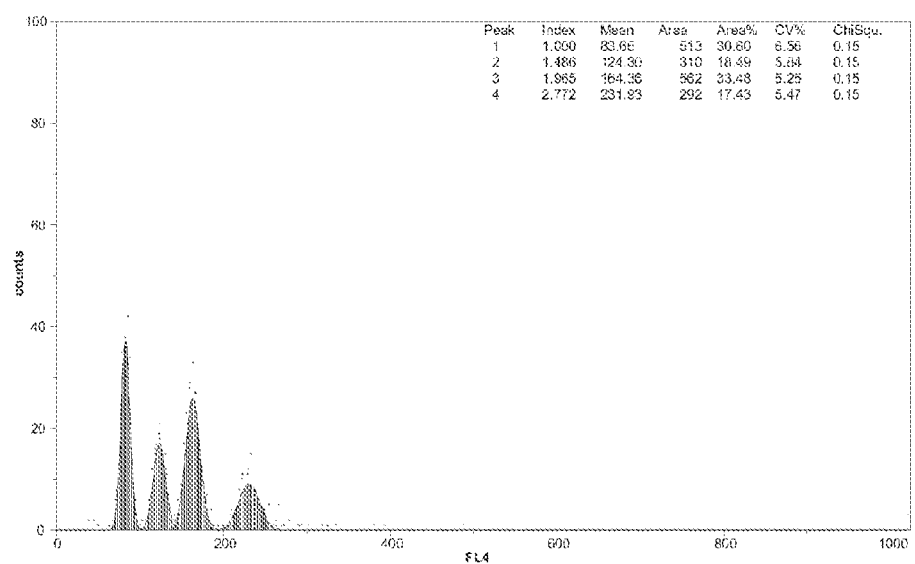
Figure 29:
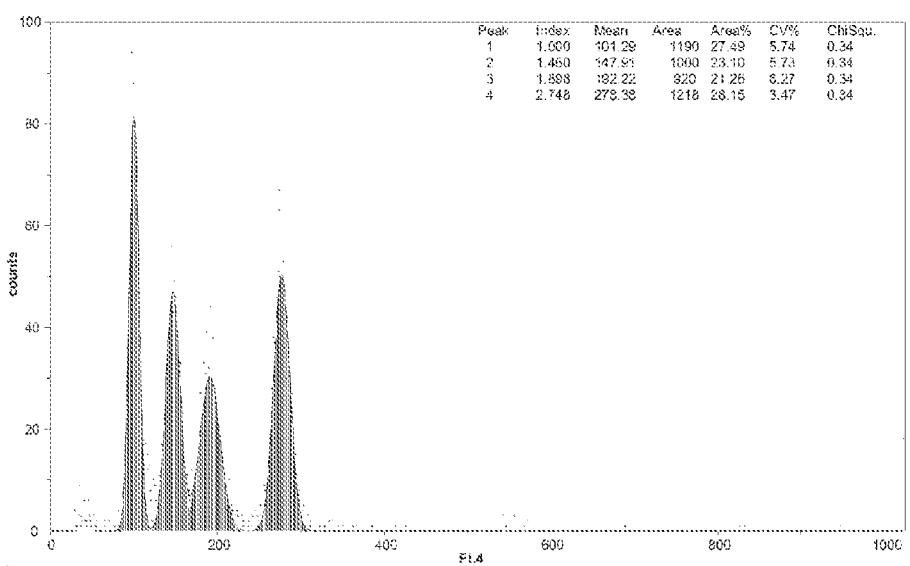

On D25 post-fertilization, a first cohort of pediveliger larvae (T≧250 μm) containing 30% of tetraploid larvae (peak "RN3" in FIG. 26, the other peaks "RN 1-2-4" corresponding respectively to the diploids, triploids, and to the internal control TRBC)) was settled on microfragments of oyster shells. This first attachment of tetraploid larvae was followed on D27 and D29 by three settlements of pediveliger larvae containing variable proportions of tetraploid larvae ranging from 20 to 40% (peaks "peak3" in FIGS. 27, 28 and 29; the other peaks "peak 1-2-4" correspond respectively to the diploid and triploid nuclei, and internal control TRBC).

EXAMPLE 2

Settlement and Development of Tetraploid Spats

1 Month Post-Settlement

Checking for the presence of tetraploid spats within the population of larvae that succeeded in metamorphosing and settling was carried out one month post-settlement, by flow cytometry. Owing to the small size of the spat at this stage, this control was carried out destructively on a sample of several spats at a time. The spats are put in a 1.5 ml tube. Then they are incubated in 1 ml of lysis buffer and are ground using a plastic plunger. Finally, the nuclei released are filtered through a nylon filter with 30 μm mesh (Partec Celltrics) and collected in a cytometry analysis tube, labeled with DAPI, and analyzed as described in Example 1 above.

Figure 30:
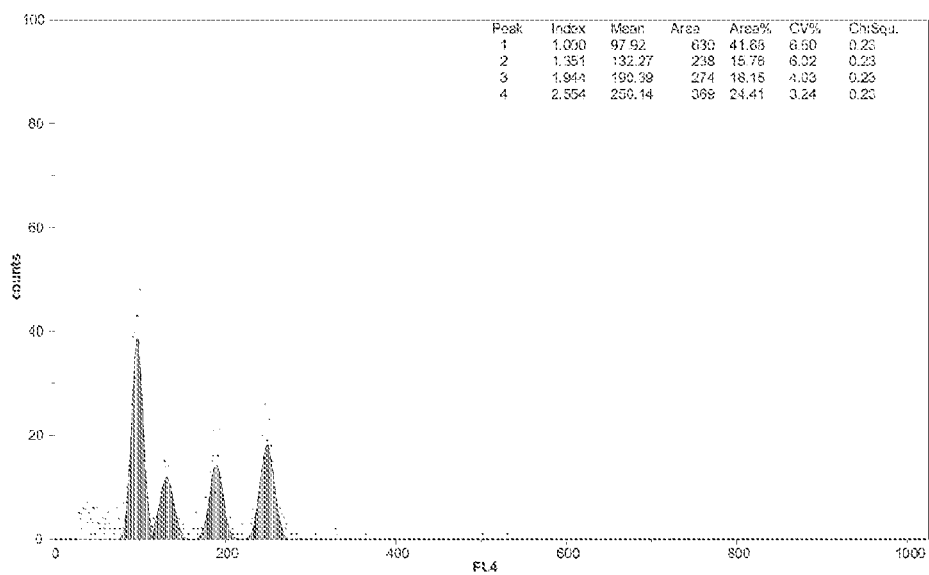
FIG. 30 shows cytometry results that confirm the presence, alongside triploid and diploid populations, of a notable population of tetraploid spats (29%) (peak 3; the peaks 1-2-4 corresponding respectively to the diploid and triploid nuclei and internal control TRBC).

The cytometry results enabled us to confirm the presence, alongside triploid and diploid populations, of a notable population of tetraploid spats (29%) ("peak3" in FIG. 30; the peaks "peak1-2-4" correspond respectively to the diploid and triploid nuclei and internal control TRBC). This population of tetraploid spats therefore succeeded in settling and continuing its development in the micronursery.

This result demonstrates the production, directly from diploid parents, of tetraploid spat that survived to the larval breeding phase and to metamorphosis permitting settlement. Moreover, the tetraploid spat obtained continues to develop even after settlement.

2 Months Post-Settlement

Two months after settlement, a check was carried out for the presence of tetraploid spats within the population of three month old spats, once again by flow cytometry, in destructive mode but on individualized spats.

Figure 31:
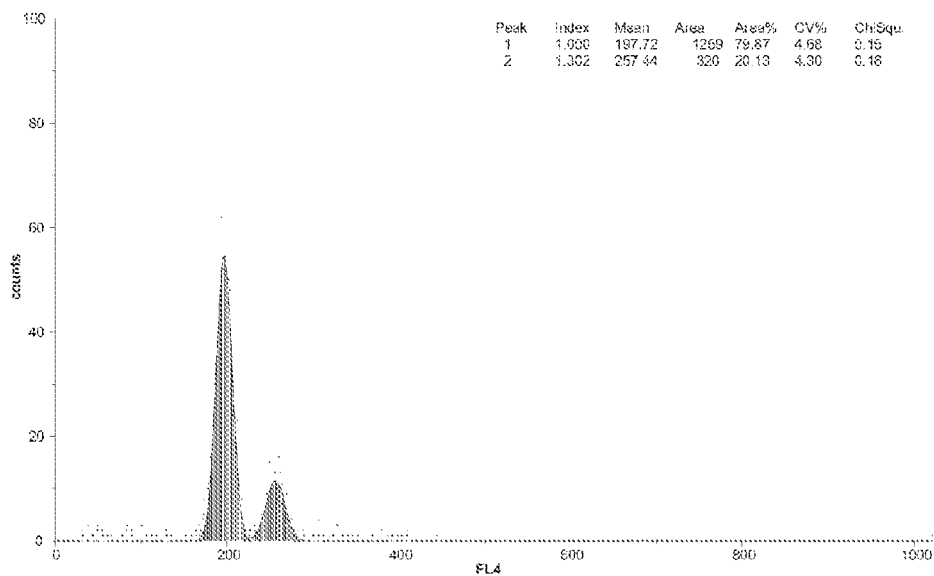
FIG. 31 shows the presence of three month old tetraploid spats.

Our results enabled us to show the presence of three month old tetraploid spats (FIG. 31). As demonstrated during larval breeding, relating the level of ploidy of an individual to its size during breeding in the micronursery also reveals differential development. In fact, the population of tetraploid spats with slow growth appears to be confined rather to the "tail of batch" and "body of batch" parts of the breeding whereas the "head of batch" part appears to be constituted of diploid and triploid spats that develop more quickly.

Thereafter, and with the aim of promoting the growth of the tetraploids, we therefore adopted the same approach as was adopted during the breeding of larvae: namely a system for sorting the spats in relation to their size and their level of ploidy so as to constitute breeding batches with the maximum possible amount of tetraploid spats and subject to the least possible competition from triploid and diploid spats.

In practice, the individualized spats underwent successive selective sievings through rectangular sieves (45×35×12 cm) with mesh ranging from 150 μm to 2 mm, passing through intermediate sizes of 350, 500 and 1000 μm.

These selective sievings were carried out at regular intervals of 15 days. According to a similar approach to that followed during the stage of breeding of larvae, "head of batch", "body of batch" and "tail of batch" populations were constituted and bred separately.

6 Months Post-Settlement

Figure 32:
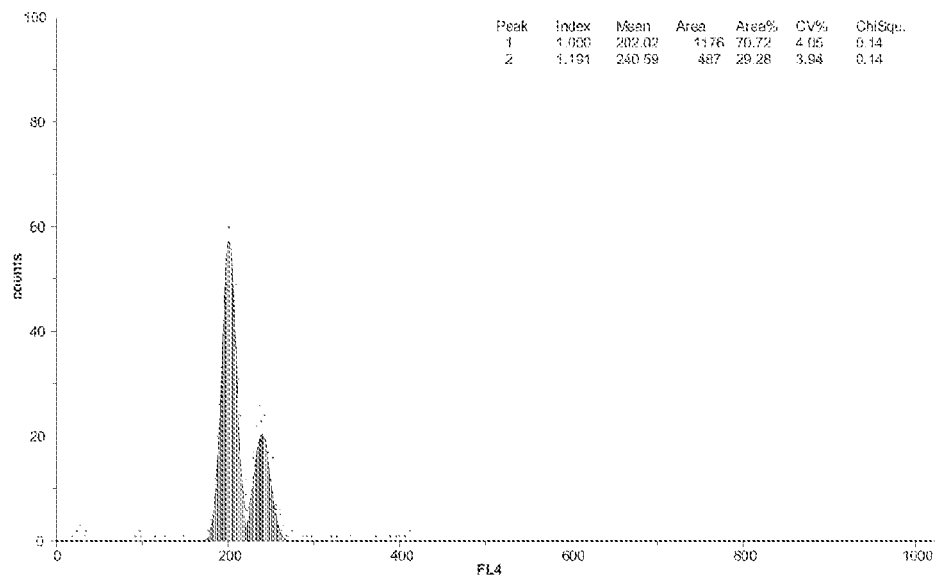
FIG. 32 shows the average proportion of 15% of tetraploid oysters directly induced from wild-type diploid parents.

At six months post-settlement, the 7-month-old spats start to be accessible for individual marking and for nondestructive testing of their level of ploidy from branchial biopsies. Thus, each individual was identified by a plastic label glued to its shell with epoxy adhesive. Then the individuals to be analyzed are anesthetized in a bath of 3 liters of seawater containing 150 g of $MgCl_2$, thus making it possible to obtain the branchial biopsy for carrying out the measurement of ploidy of the animal. At this stage, cytometric analyses performed on a total of 600 individuals have enabled us to sort more than 90 established young tetraploid oysters, on average proportion of 15% of tetraploid oysters directly induced from wild-type diploid parents (FIG. 32).

8-9 Months Post-Settlement

At eight months post-settlement, our cytometric analyses enable us to carry out sorting of more than 200 tetraploid individuals found in particular in the "tail of batch" and "body of batch" populations.

For reasons of available space, sorting of the individuals was stopped at this stage.

At nine months post-settlement, about twenty individuals with average size of 6 cm were conditioned to permit initiation of maturation and the production of gametes. These future parents were conditioned in seawater at 20° C., containing $2.10^9$ cells of phytoplankton per day and per individual. After this period of conditioning for maturation, the tetraploid parents were submitted to several shocks (thermal and of exondation) in order to trigger spawning. Of the thirty parents conditioned for maturation, 18 spawned with a sex ratio clearly favorable to the males (17 males and 1 female) which is perfectly consistent with the protandrous nature of the Pacific oyster *C. gigas*. In order to test the gametes produced by these tetraploid parents, we performed two types of crossing:

The first by fertilizing the tetraploid oocytes, obtained from the only tetraploid female, by mixing with the tetraploid sperm produced by the 17 tetraploid males.

The second by fertilizing the oocytes obtained from six wild-type diploid females with the sperm obtained from the 17 tetraploid males.

Figure 33:
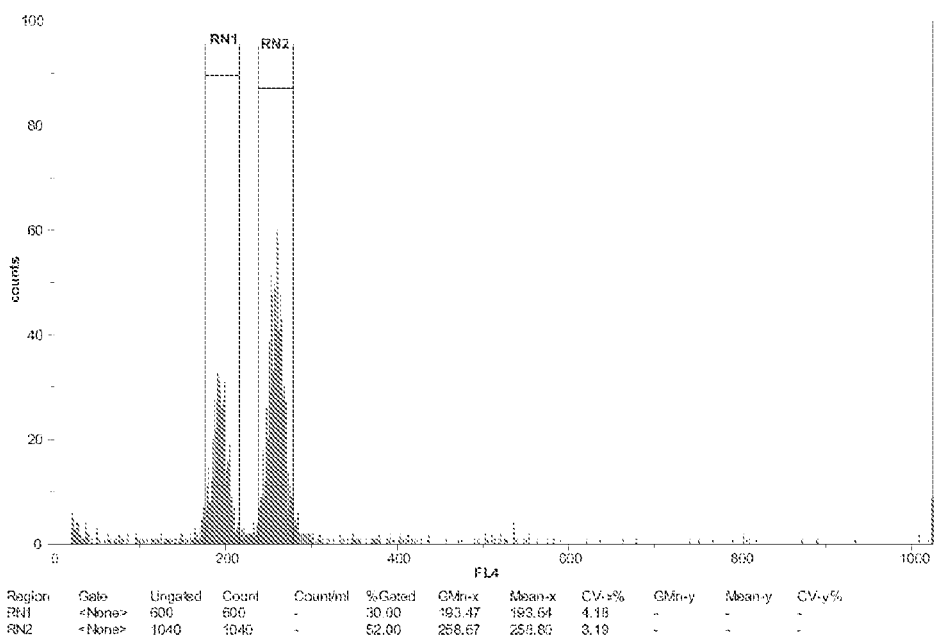
FIG. 33 shows that the new tetraploids produce only tetraploid larvae (100% of tetraploids represented by the peak RN1, the peak RN2 representing the internal control TRBC).
Figure 34:
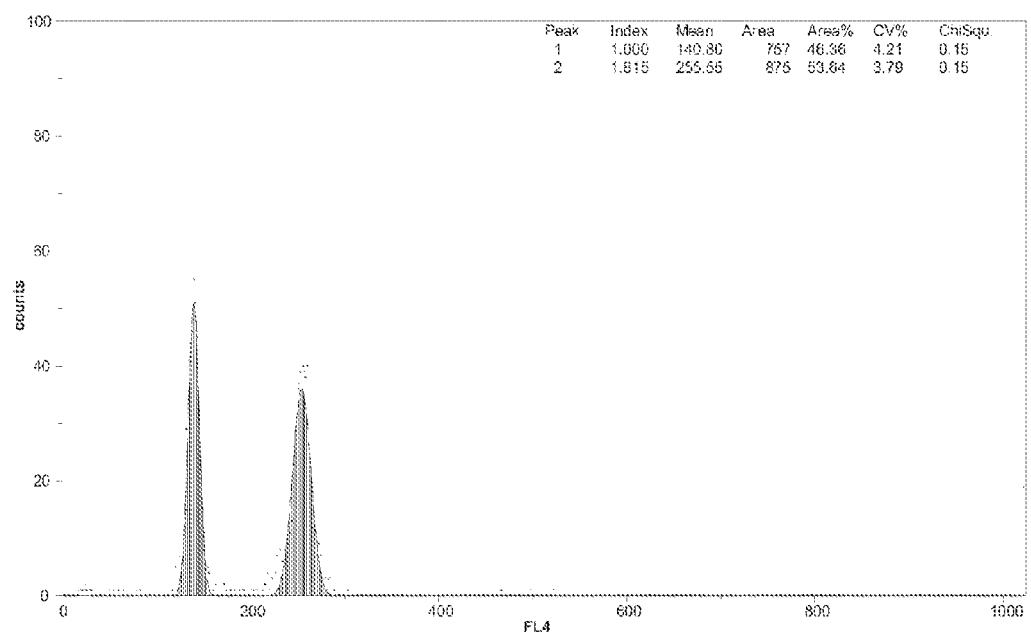
FIG. 34 shows that crossed with diploid females, the tetraploid males produce only triploid offspring (100% of triploids represented by peak 1, peak 2 representing the internal control TRBC).

Our results show clearly that the gametes produced by the parents tested are fully viable and fertilizing. Thus, crossed between them, the new tetraploids produce only tetraploid larvae (FIG. 33, 100% of tetraploids represented by the peak "RN1", the peak "RN2" representing the internal control TRBC), and crossed with diploid females, the tetraploid males produce only triploid offspring (FIG. 34, 100% of triploids represented by the peak "peak1", the peak "peak2" representing the internal control TRBC). At present, these new generations of tetraploids and of triploids have metamorphosed and settled and are being bred in the micronursery (size between 500 and 1000 μm).

In conclusion, we have succeeded in producing tetraploid oysters from diploid parents. These same tetraploids, after a conditioning treatment for gamete maturation, successfully undergo gametogenesis and are able to produce tetraploid male and female gametes that are fully viable and fertilizing. When these tetraploids were crossed with one another, they were able to produce a new generation of fully viable tetraploids. Finally, when they were used as male parents used for fertilizing diploid females, these same tetraploids produce a new generation of triploids that are also fully viable, which thus opens up a route for using these tetraploids as possible parents supplying the triploid line.

Beyond 9 Months Post-Settlement (February 2007-March 2008)

Figure 35:
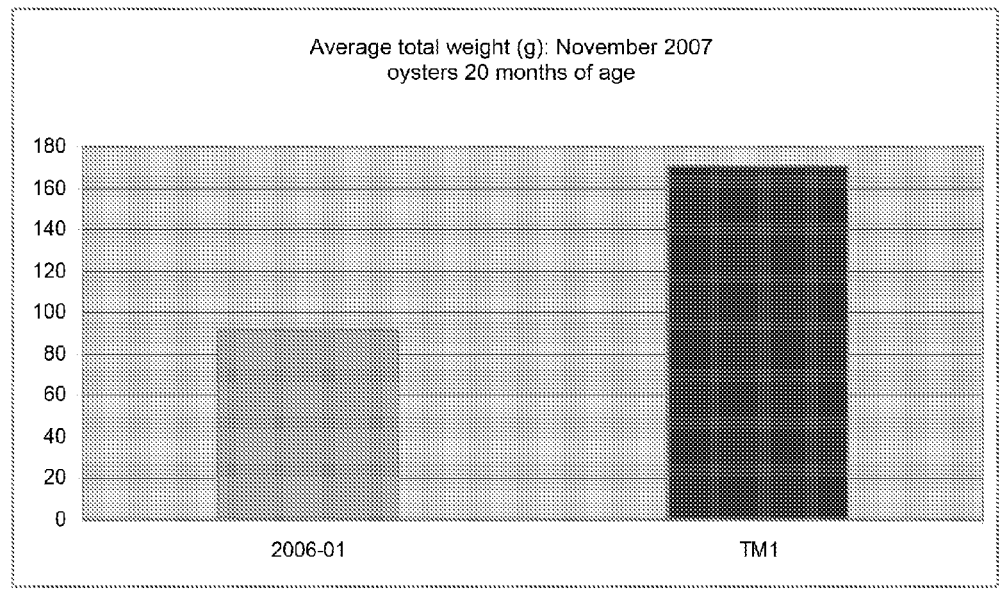
FIG. 35 shows that the first-generation of direct tetraploid oysters TM1 have even greater hardiness and weight increase.

The level of ploidy of the first-generation tetraploid oysters resulting from crossing of diploid males and females (direct tetraploid oysters, called hereinafter "TM1") is confirmed by cytometric analyses and after chromosome counting from branchial tissue using the classical karyotype techniques. Compared with conventional tetraploid oysters (i.e. those resulting from triploid females) of the same age and bred in the same conditions, the first-generation direct tetraploid oysters "TM1" have shown even greater hardiness and weight increase (FIG. 35). Thus, after twenty months of breeding, the first-generation tetraploids (TM1) are 1.86 times heavier than the conventional tetraploids (2006-01). Moreover, the TM1 stock proved to be particularly resistant since no mortality has occurred there, in contrast to the stock of conventional tetraploids (2006-01), which has suffered several mortalities, especially in summer.

Figure 36:
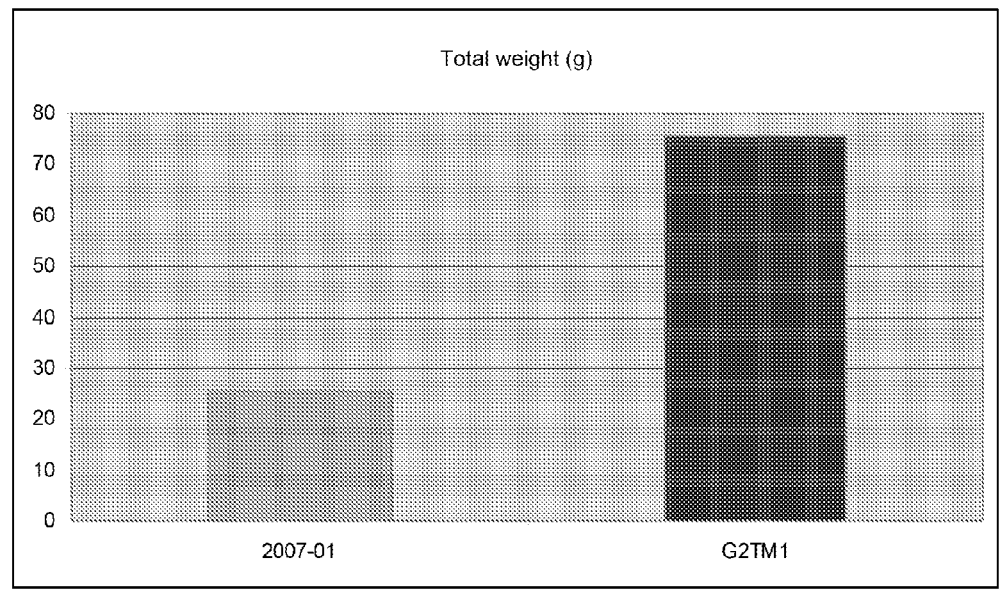
FIG. 36 shows that the G2TM1 individuals were on average 2.7 times heavier than the conventional tetraploids of the same age.

At the beginning of 2007, first-generation direct tetraploid oysters "TM1" were used as male and female parents in order to produce, following natural spawning, a second generation of direct tetraploid oysters called hereinafter "G2TM1". Tetraploidy of the G2TM1 larvae and spats was also confirmed both by cytometric analyses as well as from chromosome counts using the classical karyotype techniques. The G2TM1 spats are all tetraploid and their breeding, whether at the larval, micronursery or nursery stage, does not differ in any way from conventional breeding. During breeding, the G2TM1 spats showed very good behavior especially in terms of hardiness, growth and stability of the level of tetraploidy. Thus, compared with the conventional (i.e. resulting from triploid females) tetraploid spats (2007-01) of the same age and bred in the same conditions, even if their level of reversion to the lower levels of ploidy does not appear to be different from that presented by the conventional tetraploid spats, the G2TM1 spats display far superior growth and hardiness. In fact, after 9 months of breeding, the G2TM1 stock is composed of tetraploid individuals whose average total weight is around 75 grams whereas that of the conventional tetraploids was only around 27 grams, which means that the G2TM1 individuals were on average 2.7 times heavier than the conventional tetraploids of the same age (FIG. 36). Moreover, the G2TM1 stock has proved particularly hardy since no mortality has occurred there, in contrast to the 2007-01 stock.

Starting from November 2007, the G2TM1 tetraploids with age of 9 months post-settlement were conditioned for maturation, and two and a half months later they were used as parents to produce, by induced spawning, gametes that were used in order to produce, in February 2008, the third generation of direct tetraploids called hereinafter "G3TM1". The sex ratio of the G2TM1 tetraploid parents as well as their fertility did not differ from those of the diploid parents. The G3TM1 larvae produced are certainly tetraploid. In parallel, the G2TM1 males were also used effectively for fertilizing oocytes produced by diploid females, with the aim of producing triploids.

The above results show that the tetraploids obtained according to the invention are very effective for producing triploids. Just as with diploids, the tetraploid oysters reach maturity during their first year of age. These mature tetraploid oysters (*Crassostrea gigas* Thunberg) have a normal sex ratio and fertility comparable to that of the diploids. Crossing between tetraploids and diploids can be performed easily and normally. All the tetraploid x diploid crosses (and vice versa) produce exclusively triploid spats according to checking of ploidy by flow cytometry.

EXAMPLE 3

Production of Tetraploids in the Mussel

Tetraploids were obtained efficiently in the mussel (*M. edulis* and *Mytilus galloprovincialis*) using the procedure detailed in examples 1 and 2.

Figure 37:
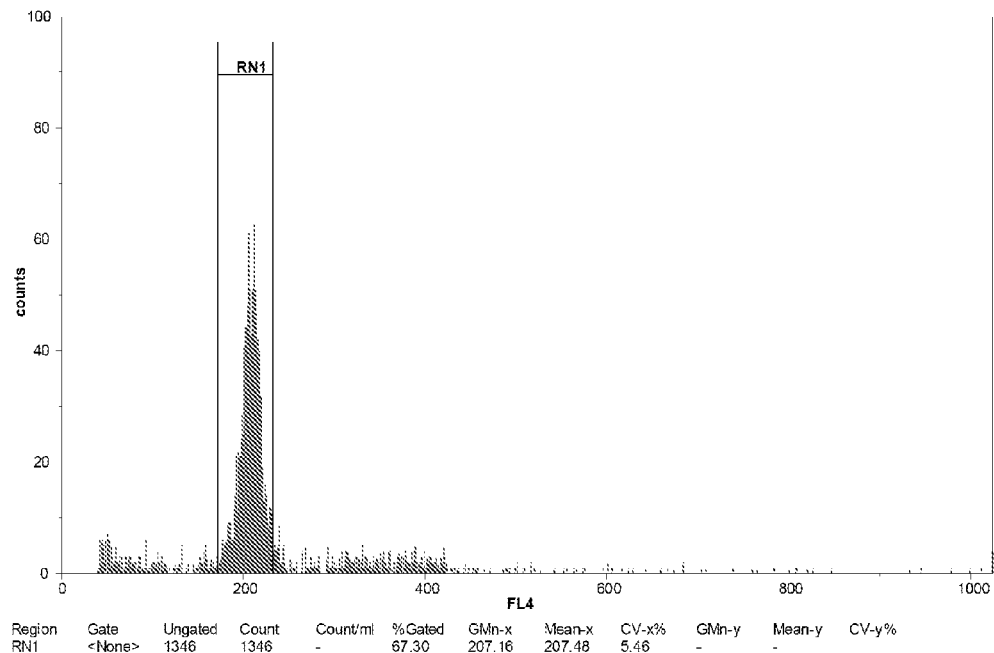
FIG. 37 shows the control crossing gives a population of exclusively diploid nuclei (peak RN 1).
Figure 38:
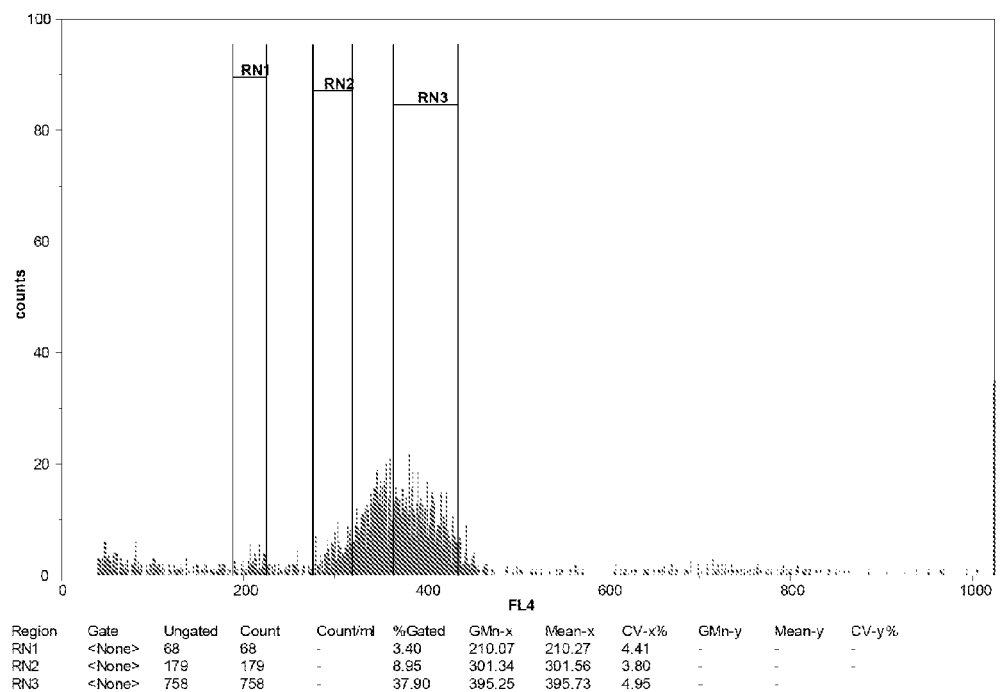
FIG. 38 shows that the samples resulting from induction of retention of GPI show three types of nuclear populations corresponding to the following levels of ploidy: diploid (around 10% on average, peak RN 1), triploid (around 20% on average, peak RN 2) and tetraploid (around 70% on average, peak RN 3).

In the mussel, the cytometry results confirmed the presence of a preponderant population of tetraploid spats, alongside triploid and diploid populations. Thus, The control crossing gives a population of exclusively diploid nuclei (FIG. 37, peak "RN 1"), The samples resulting from induction of retention of GPI show three types of nuclear populations (FIG. 38) corresponding to the following levels of ploidy: diploid (around 10% on average, peak "RN 1"), triploid (around 20% on average, peak "RN 2") and tetraploid (around 70% on average, peak "RN 3"). The tetraploid individuals obtained are in the course of being bred.

In general, and in the same way as with the Pacific oyster and the mussel, viable tetraploids can be produced in all the bivalve mollusks using the procedure detailed in the above examples.

The invention claimed is:

1. A method of producing tetraploid bivalve mollusks, characterized in that it comprises:
   a) fertilization of oocytes from diploid females with sperm from diploid males, followed by the induction of retention of the first polar body of the fertilized eggs;
   b) culture of the larvae obtained after said fertilization;
   c) isolation, from the population of larvae cultivated in stage b), of a subpopulation enriched in tetraploids, comprising at least 20% of tetraploid larvae;
   d) culture of the subpopulation of larvae isolated in stage c).

2. The method as claimed in claim 1, characterized in that the retention of the first polar body is induced by treatment with cytochalasin B, carried out between the 5th and the 25th minute after fertilization, for 10 to 20 minutes.

3. The method as claimed in claim 2, characterized in that cytochalasin B is used at a final concentration per liter of treatment medium between 0.3 and 0.7 mg.

4. The method as claimed in any one of claims 1 to 3, characterized in that the culture in stage b) is carried out for 6 to 8 days.

5. The method as claimed in any one of claims 1 to 4, characterized in that the culture in stage d) is carried out for 2 to 3 days.

6. The method as claimed in any one of claims 1 to 5, characterized in that it comprises the following additional stages:
   e) isolation, from the subpopulation of larvae cultivated in the preceding stage, of a subpopulation rich in tetraploids, comprising at least 20% of tetraploid larvae;
   f) culture of the subpopulation of larvae isolated in stage e).

7. The method as claimed in claim 6, characterized in that the culture in stage f) is carried out for 2 to 3 days.

8. The method as claimed in any one of claims 1 to 7, characterized in that the isolation of the subpopulations enriched in tetraploids is carried out by sorting the larvae on the basis of their size.

9. The method as claimed in claim 8, characterized in that the isolation of the subpopulations enriched in tetraploids is carried out by passing through a sieve of appropriate mesh, and selection of the larvae that are not retained by the sieve.

10. The method as claimed in any one of claims 1 to 9, characterized in that said bivalve mollusks are oysters.

11. The method as claimed in any one of claims 1 to 9, characterized in that said bivalve mollusks are mussels.

* * * * *